(12) United States Patent
Huang et al.

(10) Patent No.: US 10,953,059 B2
(45) Date of Patent: Mar. 23, 2021

(54) METHODS AND COMPOSITIONS FOR TREATING NON-SMALL CELL LUNG CANCER

(71) Applicant: Chang Gung Medical Foundation Keelung Chang Gung Memorial Hospital, Keelung (TW)

(72) Inventors: Tse-Hung Huang, Taoyuan (TW); Chi-Ying Huang, Taipei (TW); Hsuan-Min Hsu, New Taipei (TW); Kuan-Ting Lin, Nantou County (TW)

(73) Assignee: Chang Gung Medical Foundation Keelung Chang Gung Memorial Hospital, Keelung (TW)

( * ) Notice: Subject to any disclaimer, the term of this patent is extended or adjusted under 35 U.S.C. 154(b) by 552 days.

(21) Appl. No.: 15/579,202

(22) PCT Filed: Jun. 3, 2016

(86) PCT No.: PCT/US2016/035851
§ 371 (c)(1),
(2) Date: Dec. 2, 2017

(87) PCT Pub. No.: WO2016/197012
PCT Pub. Date: Dec. 8, 2016

(65) Prior Publication Data
US 2020/0023028 A1 Jan. 23, 2020

Related U.S. Application Data

(60) Provisional application No. 62/170,150, filed on Jun. 3, 2015.

(51) Int. Cl.
| | | |
|---|---|---|
| A61K 36/00 | (2006.01) |
| A61K 36/481 | (2006.01) |
| A61P 35/00 | (2006.01) |
| A61K 33/243 | (2019.01) |
| A61K 31/5377 | (2006.01) |
| A61K 36/232 | (2006.01) |
| A61K 36/258 | (2006.01) |
| A61K 36/284 | (2006.01) |
| A61K 36/484 | (2006.01) |
| A61K 36/488 | (2006.01) |
| A61K 36/71 | (2006.01) |
| A61K 36/725 | (2006.01) |
| A61K 36/752 | (2006.01) |
| A61K 36/756 | (2006.01) |
| A61K 36/79 | (2006.01) |
| A61K 36/88 | (2006.01) |
| A61K 36/884 | (2006.01) |
| A61K 36/9068 | (2006.01) |

(52) U.S. Cl.
CPC ........ *A61K 36/481* (2013.01); *A61K 31/5377* (2013.01); *A61K 33/243* (2019.01); *A61K 36/232* (2013.01); *A61K 36/258* (2013.01); *A61K 36/284* (2013.01); *A61K 36/484* (2013.01); *A61K 36/488* (2013.01); *A61K 36/71* (2013.01); *A61K 36/725* (2013.01); *A61K 36/752* (2013.01); *A61K 36/756* (2013.01); *A61K 36/79* (2013.01); *A61K 36/88* (2013.01); *A61K 36/884* (2013.01); *A61K 36/9068* (2013.01); *A61P 35/00* (2018.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 2002/0028253 A1 | 3/2002 | Bae et al. |
| 2011/0183015 A1 | 7/2011 | Hsieh et al. |
| 2013/0236576 A1 | 9/2013 | Lee |
| 2016/0184382 A1 | 6/2016 | Byun et al. |

FOREIGN PATENT DOCUMENTS

| | | |
|---|---|---|
| CA | 2298093 | 8/2001 |
| CN | 1235124 A | 11/1999 |
| CN | 1270699 C | 8/2006 |
| CN | 101708296 A | 5/2010 |
| CN | 103055100 A | 4/2013 |
| CN | 103948689 A | 7/2014 |
| CN | 104107388 A | 10/2014 |

(Continued)

OTHER PUBLICATIONS

Chou et al., "Oral administration of Qing-Shu-Yi-Qi-Tang reduce lung cancer-induced cachexia in mice", African Journal of Pharmacy and Pharmacology, Jan. 15, 2012, pp. 84-91, vol. 6, No. 2.

(Continued)

*Primary Examiner* — Michael V Meller
(74) *Attorney, Agent, or Firm* — Pilloff Passino & Cosenza LLP; Sean A. Passino; Rachel K. Pilloff

(57) ABSTRACT

The present invention is directed to therapeutic methods and compositions for treating non-small cell lung cancer in a subject comprising administering an effective amount of an extract or powder of a herbal mixture, optionally with an anti-cancer agent to said subject. The herbal mixture comprises a component of at least one species from each of the genus *Astragalus, Cimicifuga foetida rhizoma, Ophiopogon radix, Atractylodes lancea rhizoma, Panax ginseng*-Red, *Atractylodes rhizoma*-White, *Massa medicata fermentata, Citrus reticulata-viride, Citrus reticulata, Glycyrrhiza radix, Schisandra fructus, Angelica sinensis radix, Phellodendron cortex, Alisma rhizoma, Pueraria radix, Ziziphus fructus*-Red, and *Zingiber officinale radix*.

10 Claims, 26 Drawing Sheets

(56) References Cited

FOREIGN PATENT DOCUMENTS

| CN | 104127661 A | 11/2014 |
|---|---|---|
| CN | 104189782 A | 12/2014 |
| CN | 104225004 A | 12/2014 |
| CN | 104258046 A | 1/2015 |
| CN | 104547525 A | 4/2015 |
| WO | 2014185733 A1 | 11/2014 |

OTHER PUBLICATIONS

Michelle Whitmer, "Traditional Chinese Medicine and Lung Cancer", (Dec. 16, 2013), p. 2, URL: http://www.asbestos.com/blog/2013/12/16/traditional-chinese-medicine-herbs, (Aug. 2, 2016).

Office Action for EP Application No. 16804572.2, dated Apr. 2, 2020.

Search Report and Written Opinion for Singapore Application No. 11201709994Y, dated Nov. 25, 2019.

Xiao-Bing Yang et al., "Effect of gefitinib plus Chinese herbal medicine (CHM) in patients with advanced non-small-cell lung cancer: A retrospective case—control study," Complementary Therapies in Medicine, Oct. 12, 2014, pp. 1,010-1,018, vol. 22.

Jean Jacques Dugoua et al., "Astragalus-containing Chinese herbal combinations for advanced non-small-cell lung cancer: a meta-analysis of 65 clinical trials enrolling 4751 patients," Lung Cancer: Targets and Therapy, Jul. 8, 2010, pp. 85-100.

Search Report and Written Opinion for Singapore Application No. 11201709994Y, dated Jan. 21, 2019.

Office Action for JP Application No. 2017-563230, dated Sep. 10, 2018.

Chang Gung Memorial Hospital, "Effect of Astragalus-based Formula: Qingshu-Yiqi-Tang on Modulating Immune Alterations in Lung Cancer Patients (QSYQT)," Mar. 1, 2013, ClinicalTrials.gov.

Hang Wang et al, "Improving Cachectic Symptoms and Immune Strength of Tumour-Bearing Mice in Chemotherapy by a Combination of Scutellaria Baicalensis and Qing-Shu-Yi-Qi-Tang," European Journal of Cancer, Jul. 23, 2011, pp. 1,074-1,084, vol. 48, No. 7.

Yu-He Zou et al., "Effect of Astragalus Injection Combined With Chemotherapy on Quality of Life in Patients With Advanced Non-Small Cell Lung Cancer," Oct. 2003.

Extended European Search Report for EP Application No. 16804572.2, dated Jan. 8, 2019.

Database WPI, Derwent World Patents Index, vol. 2014, No. 80, Database accession No. 2014-U82300, XP002787250.

Database WPI, Derwent World Patents Index, vol. 2015, No. 20, Database accession No. 2015-16389U, XP002787147.

Database WPI, Derwent World Patents Index, vol. 2015, No. 04, Database accession No. 2015-03812V, XP002787148.

Database TCM [Online], SIPO; Nov. 17, 1999 (Nov. 17, 1999), XP002787149, Database accession No. CN-98117365-A; & CN 1 235 124 A (ILL JU.

Database WPI, Derwent World Patents Index, vol. 2010, No. 39, Database accession No. 2010-F97091, XP002787251.

Database WPI, Derwent World Patents Index, vol. 2015, No. 29, Database accession No. 2015-26666T, XP002787252.

Database WPI, Derwent World Patents Index, vol. 2013, No. 65, Database accession No. 2013-P86069, XP002787253.

Database WPI, Derwent World Patents Index, vol. 2015, No. 19, Database accession No. 2015-113798, XP002787254.

Qing Shu Yi Qi Tang Jia Jian—Modified Clear Summerheat and Augment Qi Decoction,' American Dragon, (2011-2017), [Online], Viewed online May 21, 2020, Printed May 27, 2020, <URL:https://www.americandragon.com/Herb%20Formulas%20copy/QingShuYiQiTangJiaJian.html>.

Examination Report for AU Application No. 2016270375, dated May 21, 2020.

J. Unknown Doe, "Advances in clinical and experimental researches on inhibiting non-small cell lung cancer with traditional Chinese medicine", published at http://www.39kf.com/cooperate/lw/zxjh/01/2012-12-24-850951.shtml on Dec. 24, 2012 (4 pages).

J. Unknown Doe, entitled "Injection of Astragalus solution in patients receiving chemotherapy to improve the quality of treatment" Published at https://blog.udn.com/wrjobik/9441784, on Nov. 12, 2013 (2 pages).

"Clinical Examples of Qing-Shu-Yi-Qi-Tang," published in Shaanxi Zhongyi, 2010 vol. 31(3) p. 358.

"Selected Cases of Chinese Internal Medicine" 1st edition, editor Xiaoping Zhang, Mingren Chen, Publisher: Shanghai University of Traditional Chinese Medicine Press, published in Sep. 2001, pp. 80-81.

"Oncology diagnosis and treatment strategy" 2nd edition, editor: Jin Li, published by Shanghai Science and Technology Press, published in Jun. 2010, p. 49.

"Chinese Prescriptions Collection" 2nd edition, editor: Ang Wang et al., published by China Press of Traditional Chinese Medicine Co., Ltd, published in May 2007, p. 150.

"Practical diagnosis and comprehensive treatment of common tumors" 1st edition, editor: Zongwen Liu and Weiwei Tian, published by Zhengzhou University Press, published in Dec. 2014, pp. 172-173. (A4).

Office action issued in corresponding Taiwan application, dated Mar. 13, 2017.

Chinese Journal of Integrated Traditional and Western Medicine or CJITWM, Oct. 2003 vol. 23, No. 10, pp. 733-735. (Translation of Table 1 enclosed.).

Office Action for Japan Application No. 2019-132291, dated Aug. 18, 2020.

FIG. 1A/1B
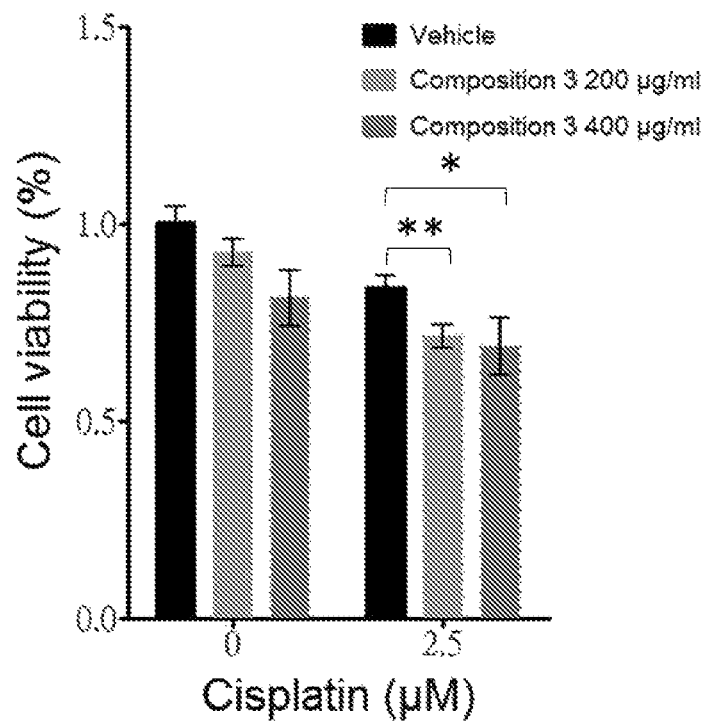
1A
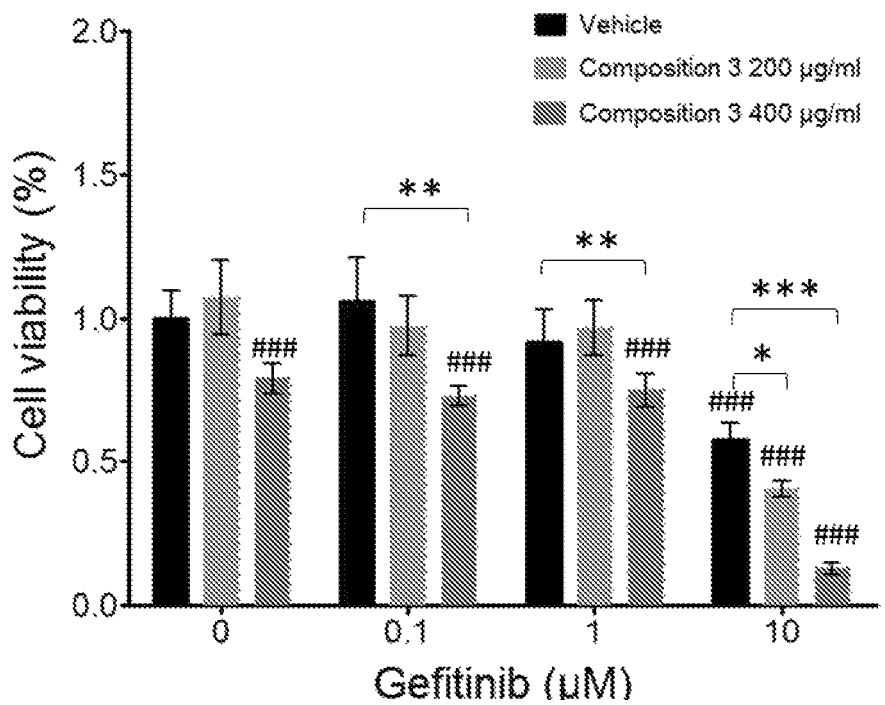
1B

FIG. 3A
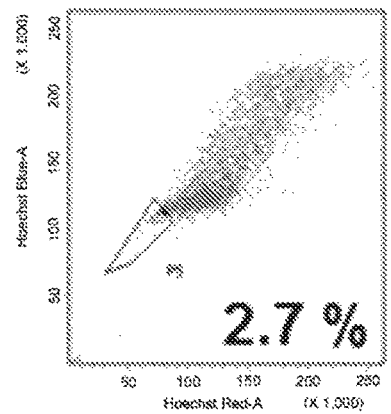
Hoechst — 2.7 %
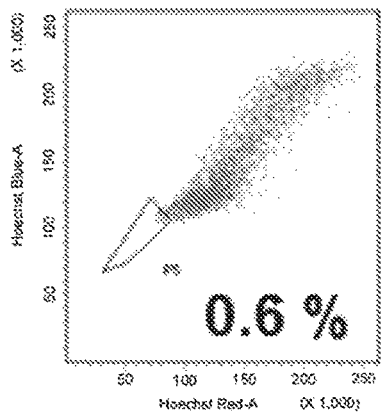
AM-decoction-H$_2$O 100 μg/ml — 0.6 %
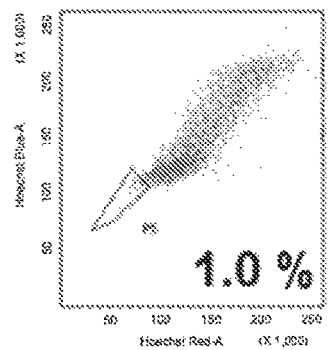
AM-decoction-DMSO 100 μg/ml — 1.0 %
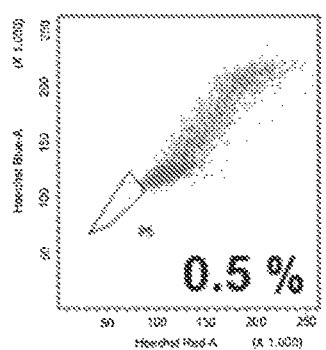
Composition 4 200 μg/ml — 0.5 %
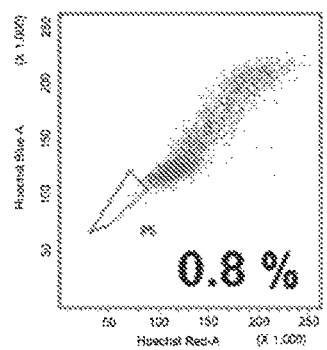
Composition 5 200 μg/ml — 0.8 %

FIG. 4A/B
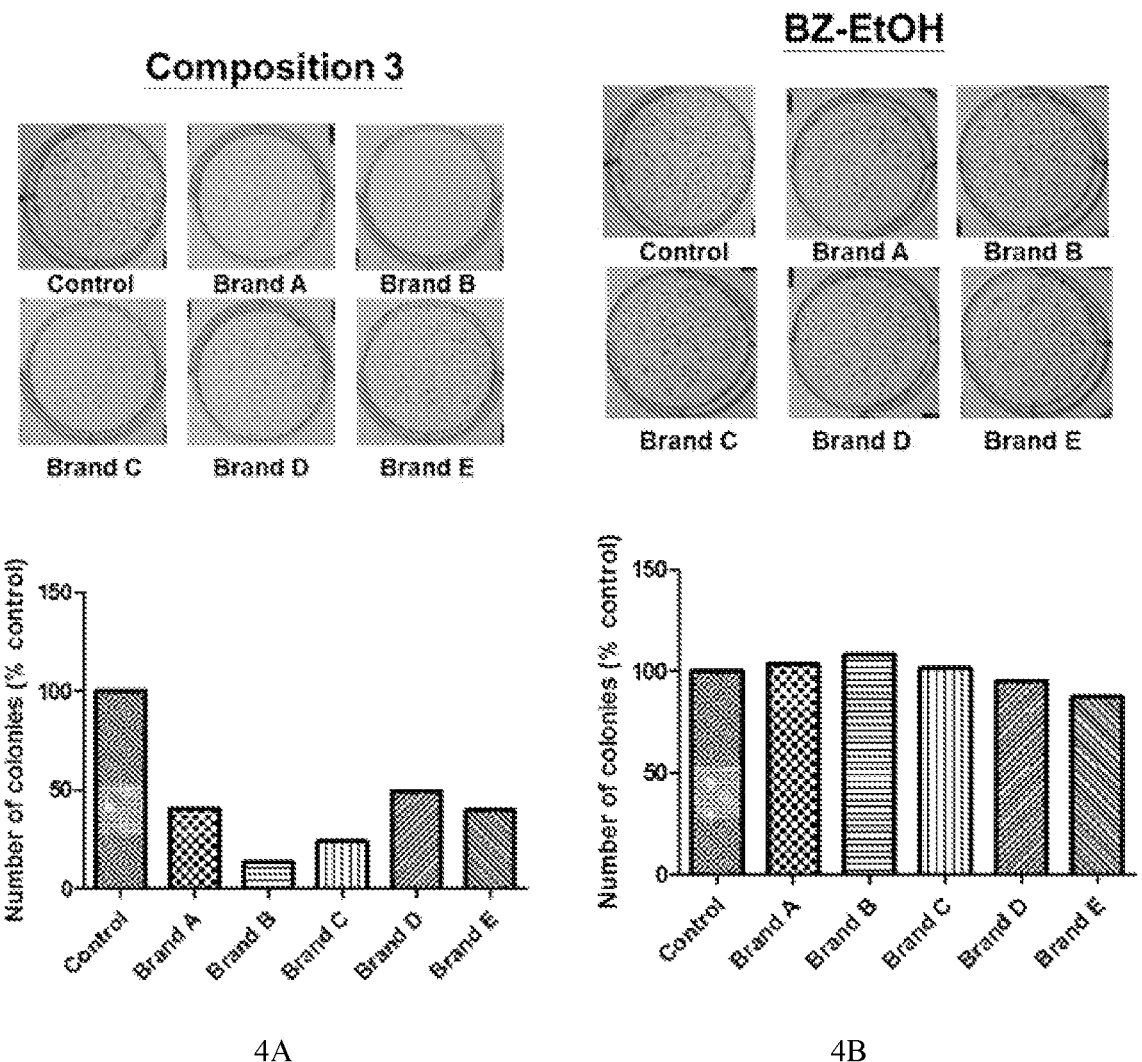

FIG. 4C/D
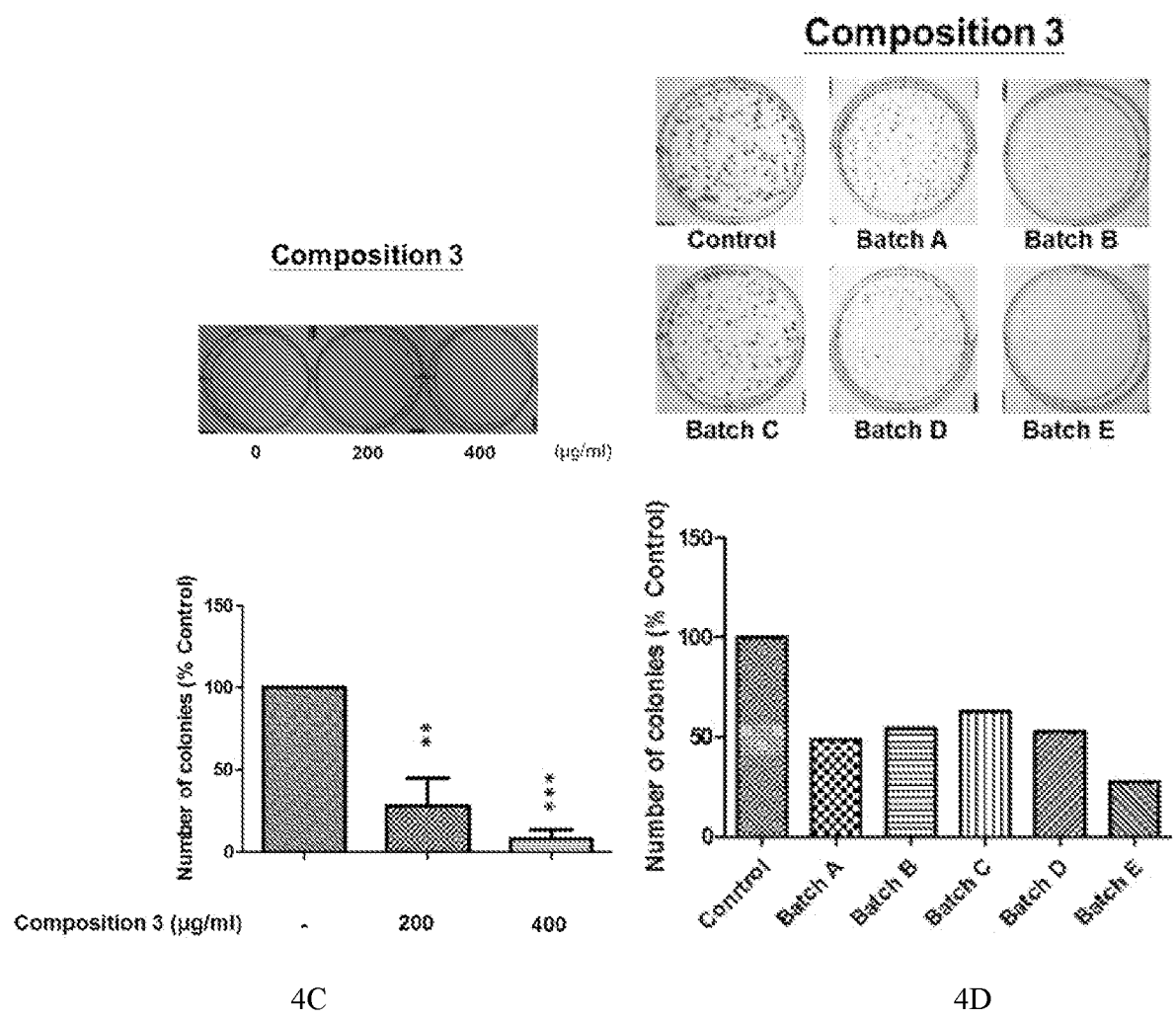
4C
4D

FIG. 5A/B
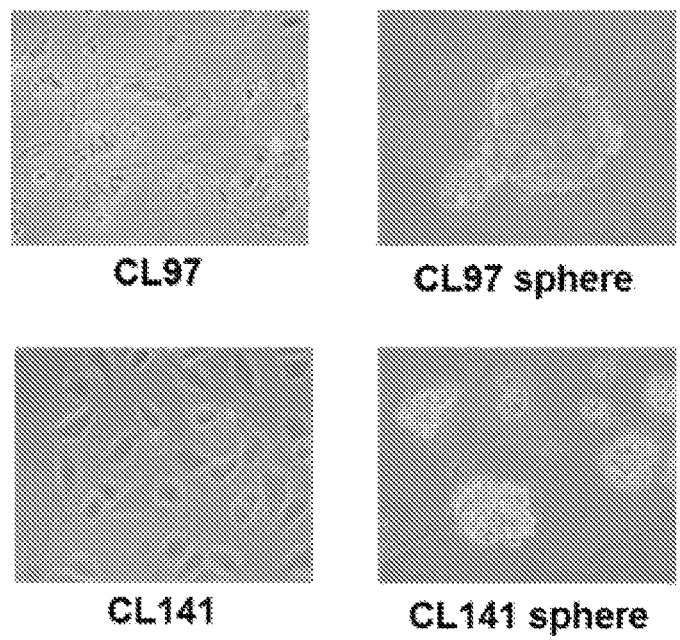
5A
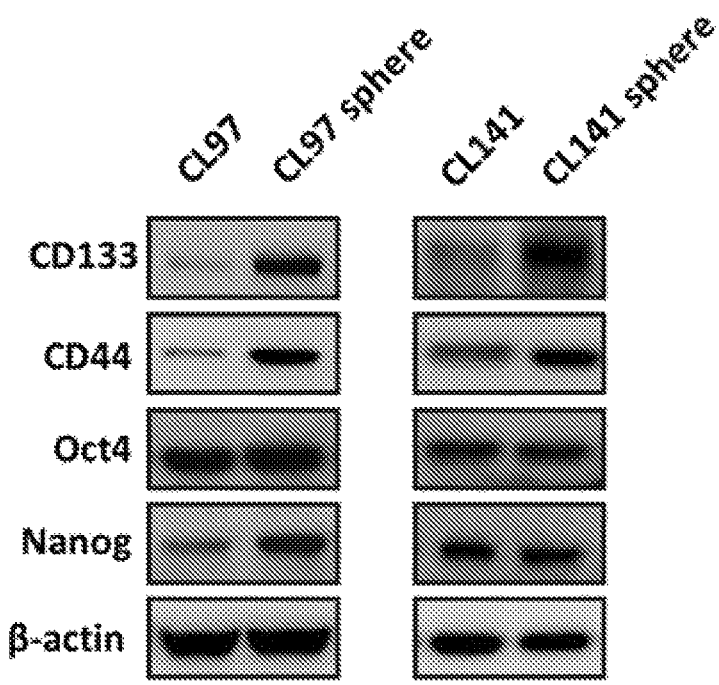
5B

FIG. 5C/D
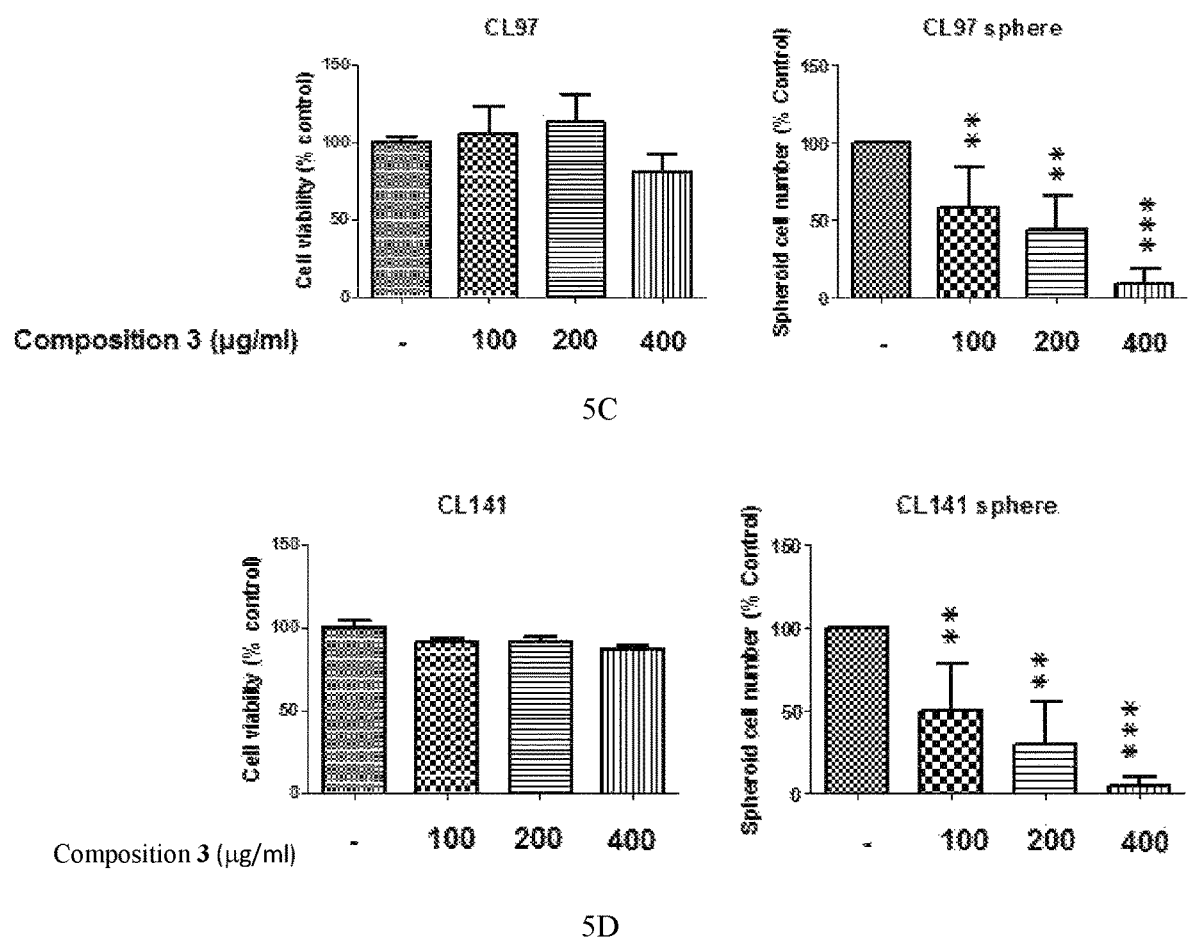
5C
5D

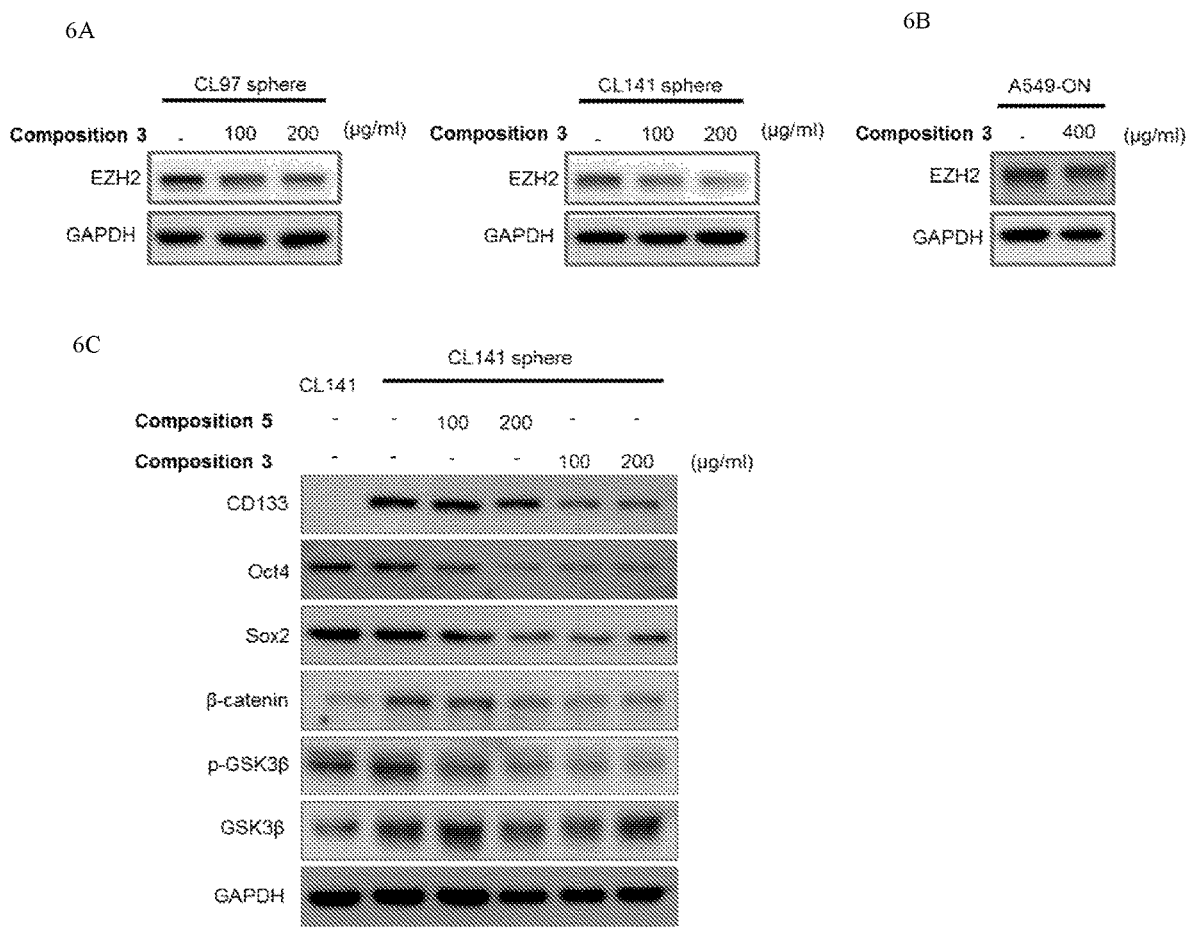
FIG. 6A-C

FIG. 7A/B
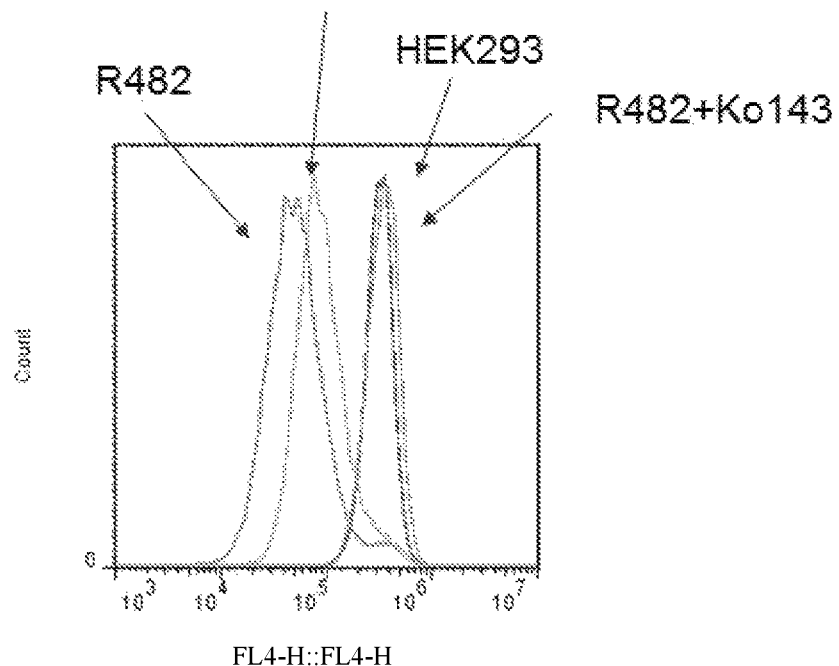
7A
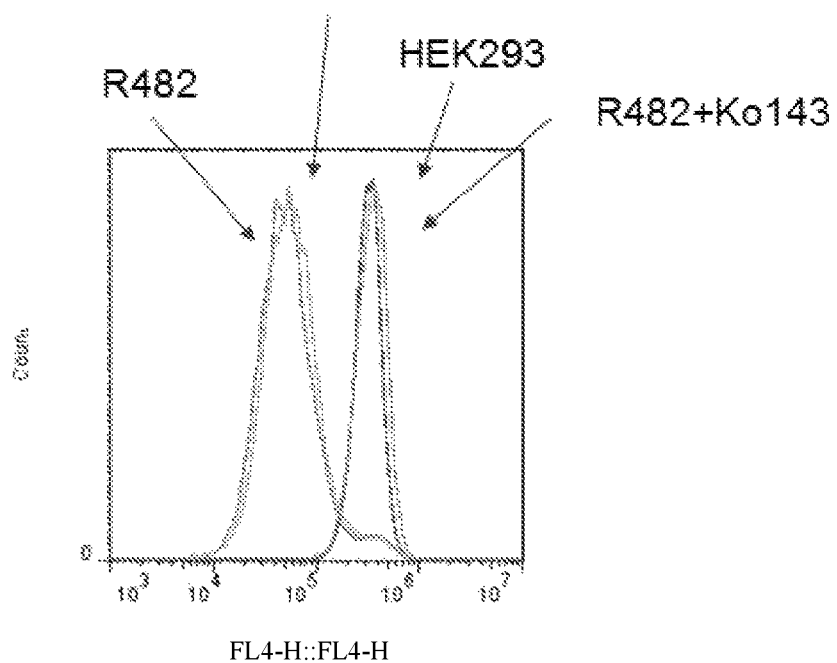
7B

FIG. 8A/B
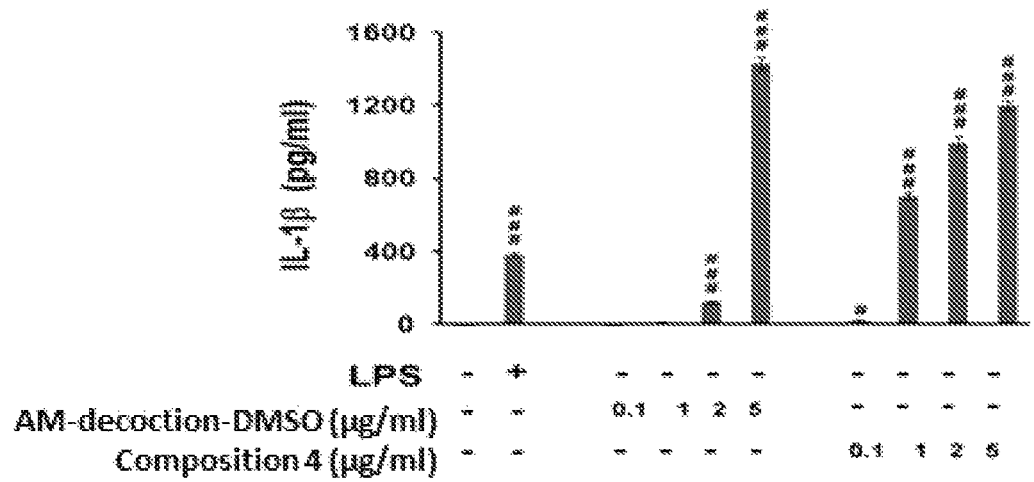
8A
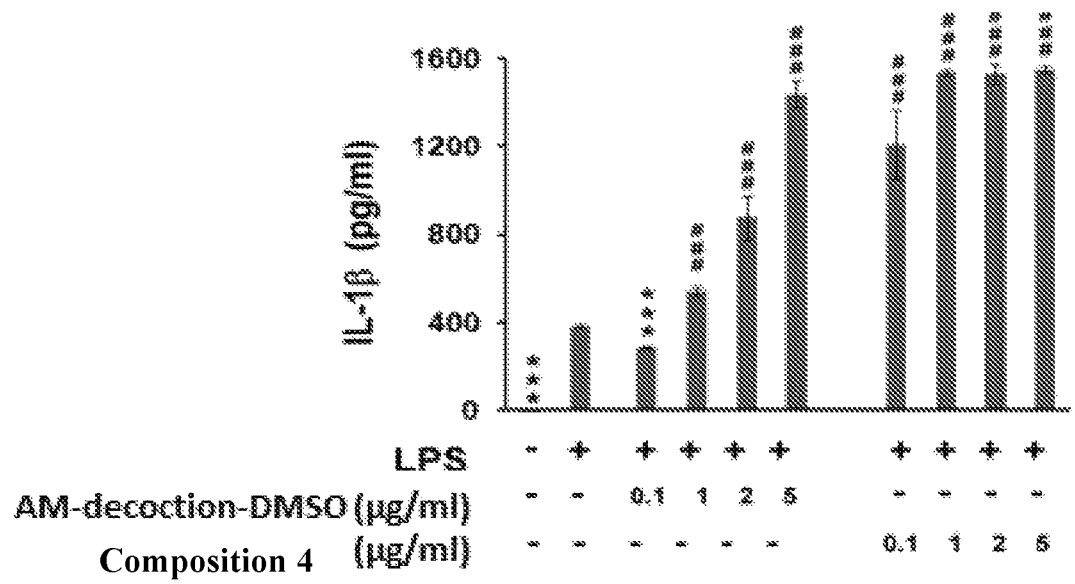
8B

FIG. 8C/D
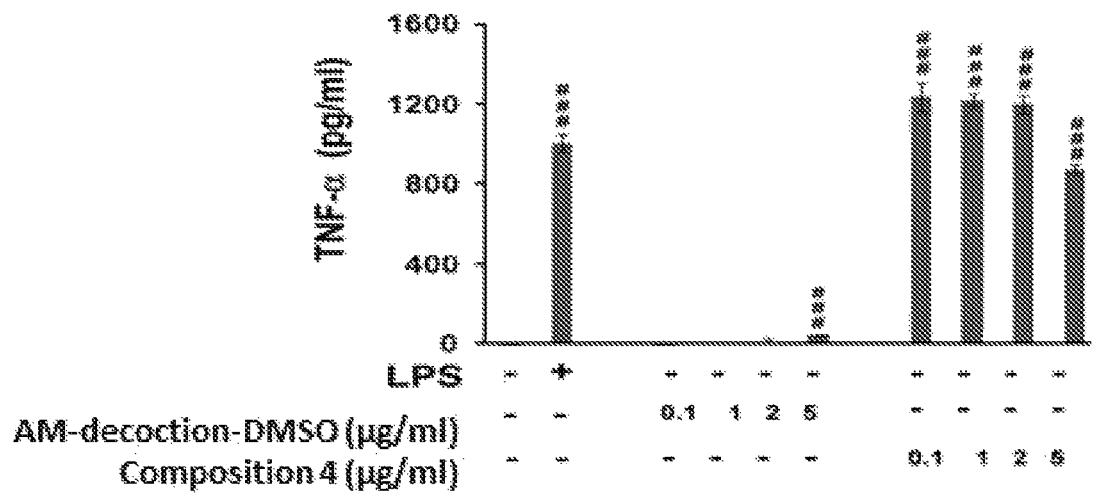
8C
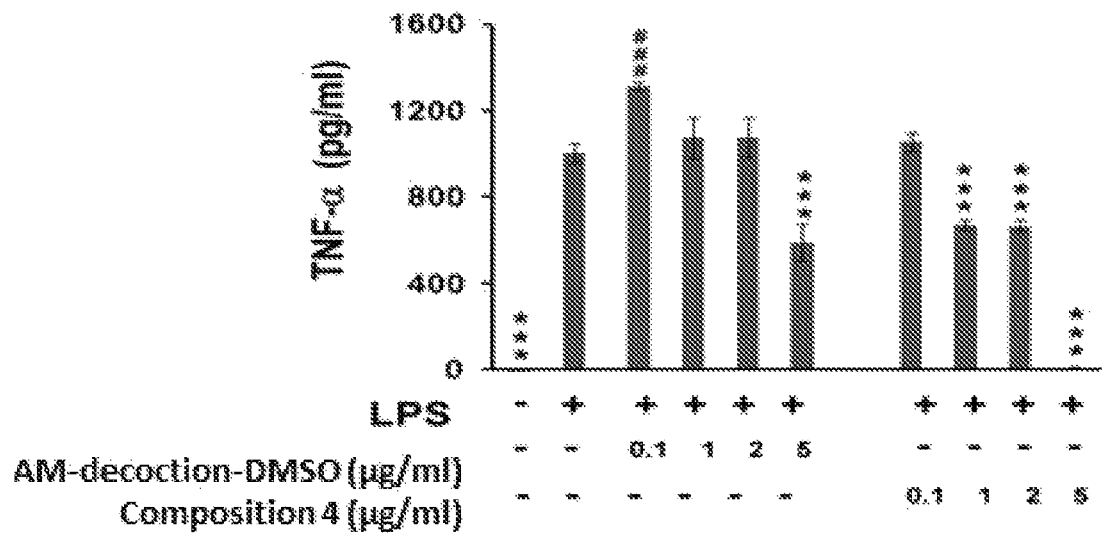
8D

FIG. 9A-C
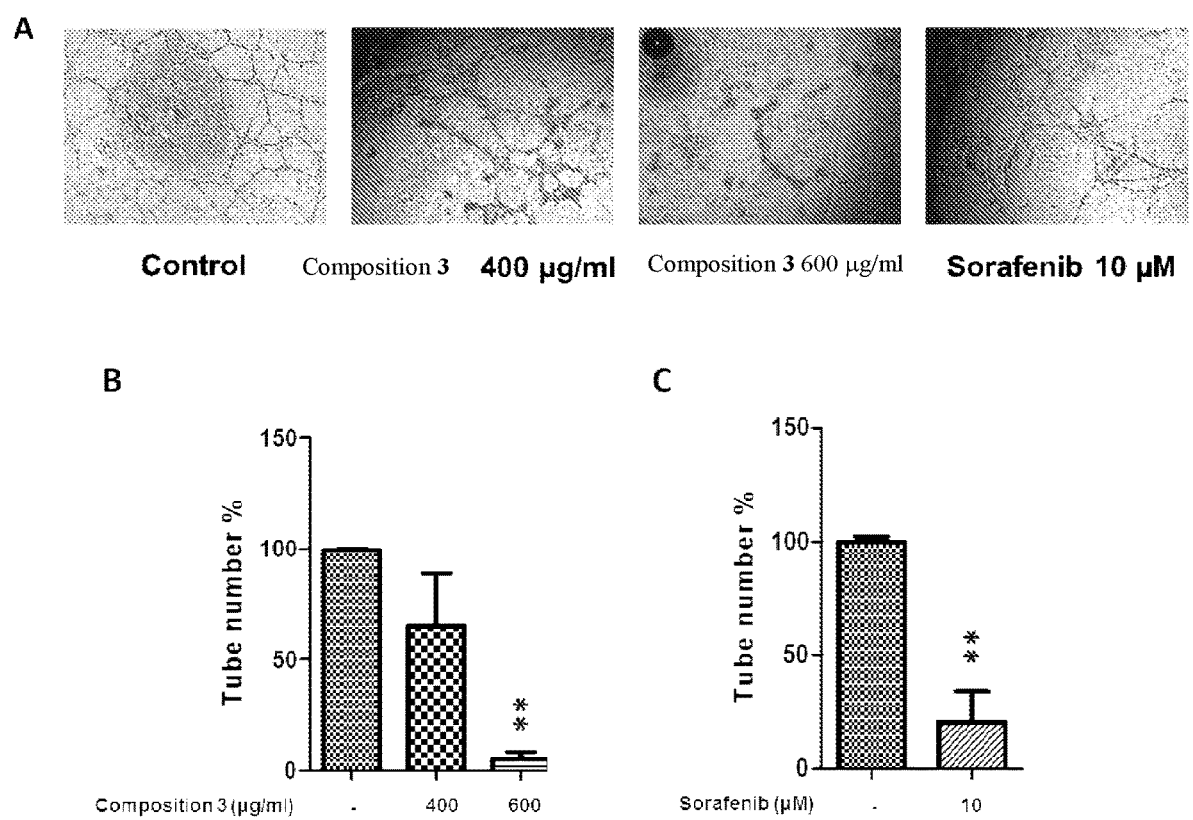

FIG. 10A/B
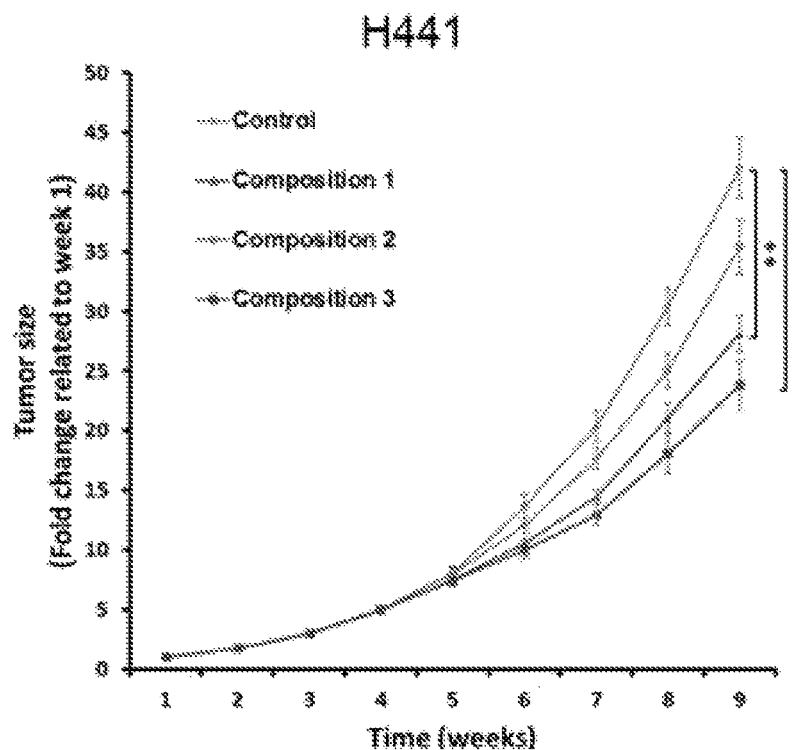
10A
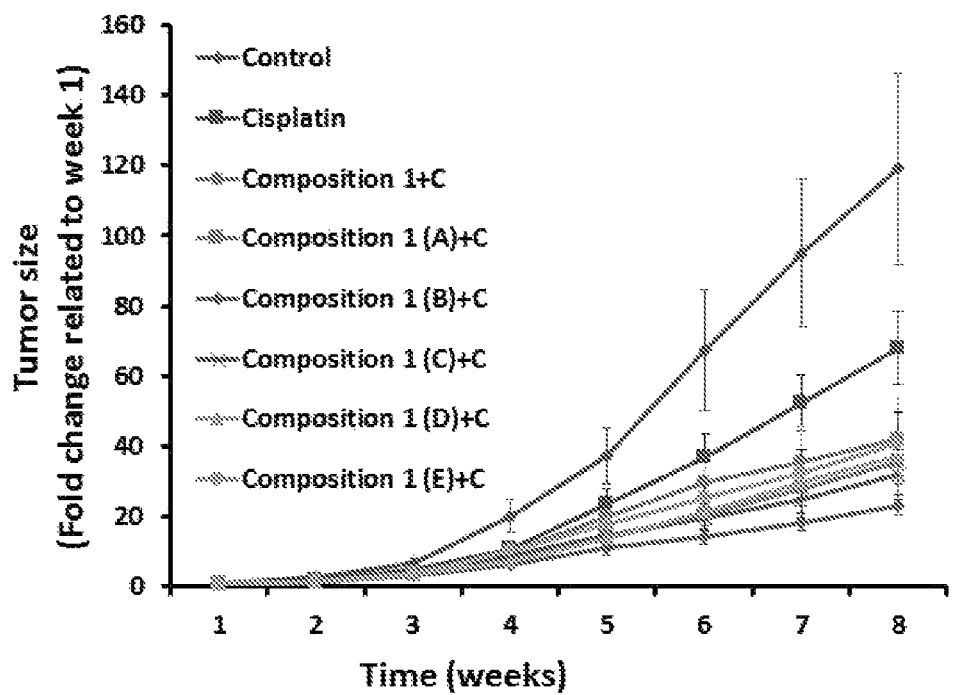
10B

FIG. 12A/B
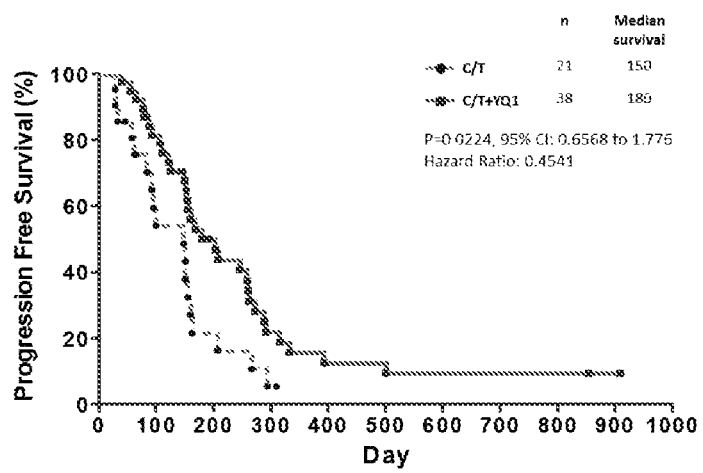
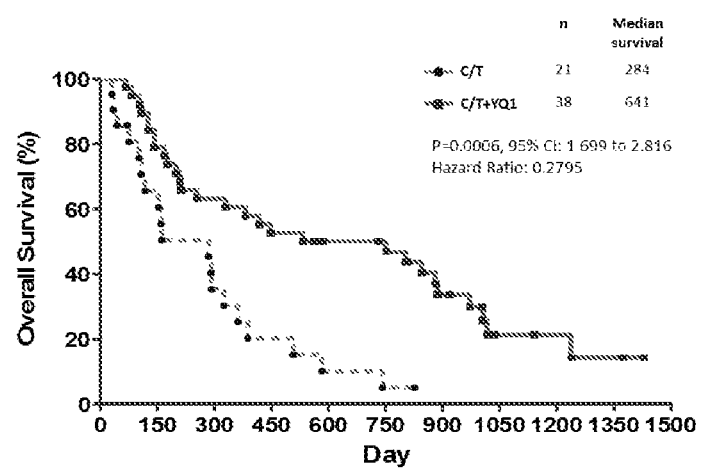

FIG. 12C/D
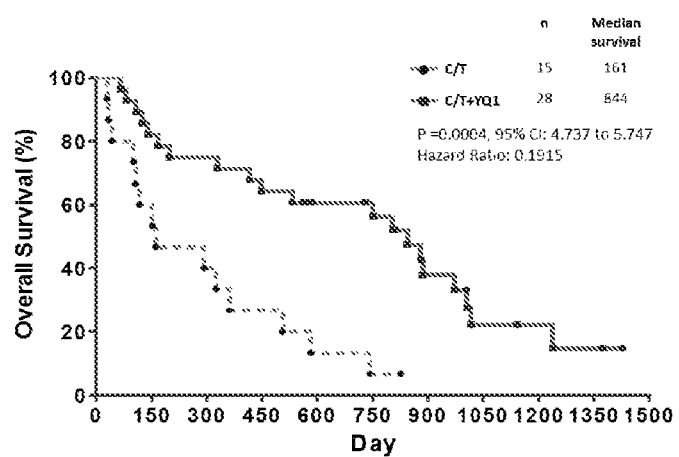
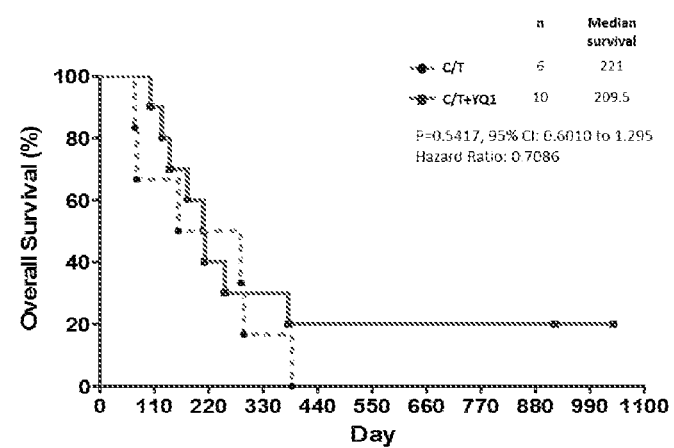

FIG. 12E/F
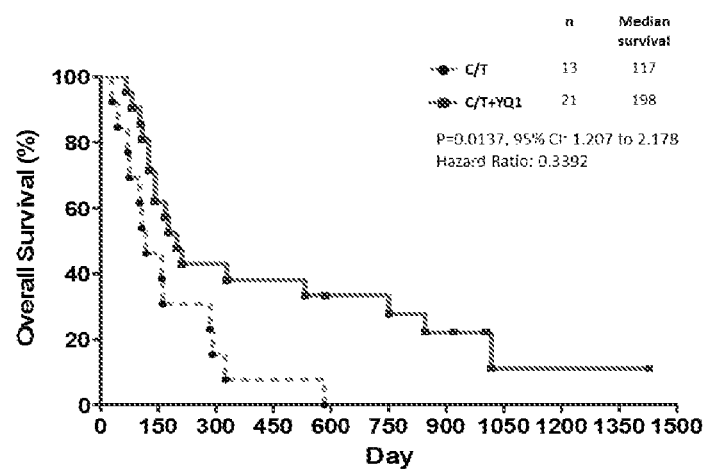
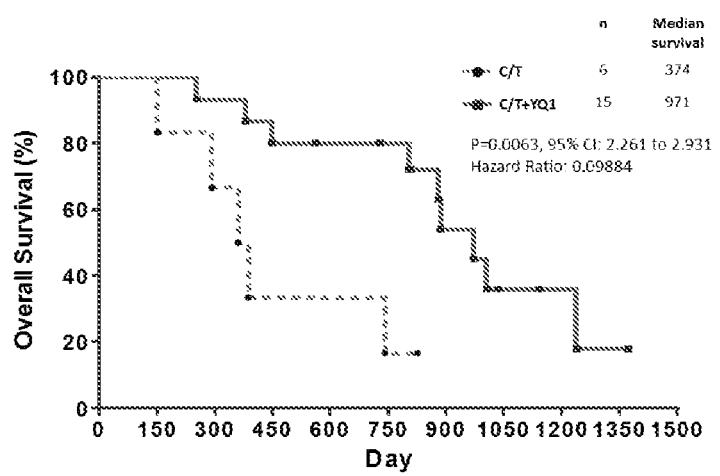

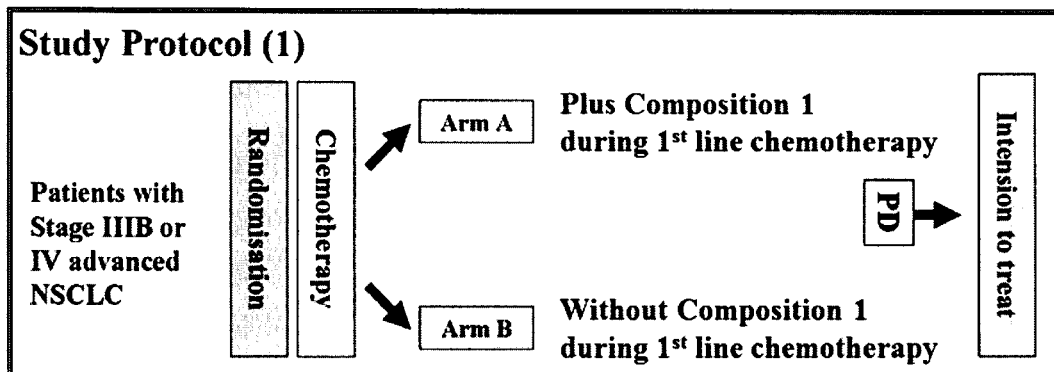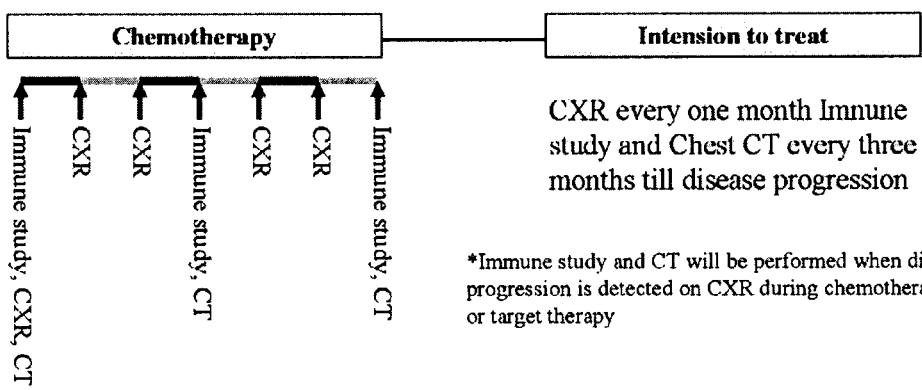
FIG. 17

METHODS AND COMPOSITIONS FOR TREATING NON-SMALL CELL LUNG CANCER

BACKGROUND OF THE INVENTION

Lung cancer is a disease which consists of uncontrolled cell growth in tissues of the lung. This growth may lead to metastasis, which is the invasion of adjacent tissue and infiltration beyond the lungs. The vast majority of primary lung cancers are carcinomas, derived from epithelial cells. Lung cancer, the most common cause of cancer-related death in men and women, is responsible for 1.3 million deaths worldwide annually, as of 2004. Common treatments for lung cancer include palliative care, surgery, chemotherapy, radiation therapy (radiotherapy) and target therapy.

The main types of lung cancer are small cell lung cancer (SCLC) and non-small cell lung cancer (NSCLC). Small cell lung cancer (SCLC) is a fast-growing type of lung cancer. It spreads much more quickly than non-small cell lung cancer. There are three different types of small cell lung cancer: small cell carcinoma (oat cell cancer), mixed small cell/large cell carcinoma and combined small cell carcinoma. Most small cell lung cancers are the oat cell type. Non-small cell lung cancer (NSCLC) is the most common type of lung cancer. There are three forms of NSCLC: adenocarcinomas, squamous cell carcinomas and large cell carcinomas. Also there are several other types that occur less frequently, and all types can occur in unusual histologic variants and as mixed cell-type combinations. Adenocarcinomas are often found in an outer area of the lung. Squamous cell carcinomas are usually found in the center of the lung by an air tube (bronchus). Large cell carcinomas can occur in any part of the lung. They tend to grow and spread faster than the other two types. Sometimes the phrase "non-small-cell lung cancer" ("not otherwise specified", or NOS) is used generically, usually when a more specific diagnosis cannot be made. This is most often the case when a pathologist examines a small amount of malignant cells or tissue in a cytology or biopsy specimen.

As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy).

SUMMARY OF THE INVENTION

In one aspect provided herein are compositions for treating non-small cell lung cancer in a subject comprising an extract or powder of a herbal mixture, and an anti-cancer agent, wherein said herbal mixture comprises a component of at least one species from each of the genus *Astragalus, Cimicifuga foetida rhizoma, Ophiopogon radix, Atractylodes lancea rhizoma, Panax ginseng*-Red, *Atractylodes rhizoma*-White, *Massa medicata fermentata, Citrus reticulata-viride, Citrus reticulata, Glycyrrhiza radix, Schisandra fructus, Angelica sinensis radix, Phellodendron cortex, Alisma rhizoma, Pueraria radix, Ziziphus fructus*, and *Zingiber officinale radix*.

In another aspect provided herein are methods for treating non-small cell lung cancer in a subject comprising administering an extract or powder of a herbal mixture, optionally with an anti-cancer agent to a subject, wherein said herbal mixture comprises a component of at least one species from each of the genus *Astragalus, Cimicifuga foetida rhizoma, Ophiopogon radix, Atractylodes lancea rhizoma, Panax ginseng*-Red, *Atractylodes rhizoma*-White, *Massa medicata fermentata, Citrus reticulata-viride, Citrus reticulata, Glycyrrhiza radix, Schisandra fructus, Angelica sinensis radix, Phellodendron cortex, Alisma rhizoma, Pueraria radix, Ziziphus fructus*, and *Zingiber officinale radix*.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-C show illustrative results of cell line cytotoxicity study of the combination therapy of Composition 3 with cisplatin or gefitinib. (2A) Combination treatment of cisplatin and Composition 3 in CL141 lung cancer cells at 48 hrs. Combination treatment of gefitinib and Composition 3 in (2B) CL141 and (2C) CL97 lung cancer cells at 72 hrs. (t-test, *: p value<0.05; : p value<0.01; *: p value<0.001 compared with different dosages of Composition 3 at the same dosage of cisplatin or gefitinib. #: p value<0.05; ##: p value<0.01; ###: p value<0.001 compared different treatments with vehicle control.)

FIG. 3A-B show illustrative results of the cancer stem cell survival study of Composition 3, Composition 4, Composition 5, AM-Decoction-$H_2O$, and AM-Decoction-DMSO. (3A) The side population cells of CL141 with Composition 4, Composition 5, AM-Decoction-$H_2O$, and AM-Decoction-DMSO; (3B) the side population of lung cancer cell lines CL97, CL141, and H441 with Composition 3.

FIG. 4A-D show illustrative study results of non-small cell lung carcinomas A549 colony formation inhibition by Compositing 3. (4A) Colony formation results of five different brands (brand A-brand E) with Composition 3 (200 μg/ml). (4B) Colony formation results of five different brands (brand A-brand E) with BZ-EtOH (200 μg/ml). (4C) Colony formation results of a particular brand with Composition 3 in concentration of 200 μg/ml or 400 μg/ml. (4D) Colony formation results of five different batches from the same brand (batch A-batch E) with Composition 3.

FIG. 5A-D show illustrative study results of cancer stem-like cell survival study by Composition 3. (5A) Cell morphology of parental CL97 and CL141 cells and anchorage independent culture of CL97 and CL141 sphere cells. (5B) Western blot results of the expression of stemness markers in CL97 and CL141 parental and sphere cells. (5C, 5D) The results of CL97 and CL141 secondary sphere cells treated with different concentrations of Composition 3 for 48 hrs (Control cells were treated with DMSO and used as 100%). (t-test, *: p value<0.05; : p value<0.01;*: p value<0.001)

FIG. 6A-C show illustrative study results of stemness markers and Wnt target expression by Compositions 3 or 5. (6A) Composition 3 over CL97 and CL141 sphere. (6B) Composition 3 over A549-ON. (6C) Compositions 3 and 5 over CL141 sphere.

FIG. 7A-B show illustrative results of ABCG2 transport activity inhibition study with Compositions 2 and 3 by western blot. The accumulation of fluorescent pheophorbide-A (PhA) in drug-sensitive parental HEK293 cells or ABCG2-transfected HEK293 cells (referred to as R482-HEK293) was measured in the absence or presence of Composition 3 (200 μg/ml) (7A) and Composition 2 (200 μg/ml) (7B).

FIG. 8A-D show illustrative immune response studies of Composition 4 and AM-Decoction-DMSO (8A) for production of IL-1 β expression in human THIP-1 macrophages, (8B) production of IL-1 β after co-treated with LPS, (8C) production of TNF-α expression in human THP-1 macrophages, and (8D) production of LPS-stimulated of TNF-α expression.

FIG. 9A-C show illustrative results of the tube formation assay of Composition 3 in HUVEC cells.

FIG. 10A-C show illustrative results of the preclinical anti-tumor evaluation of Compositions 1, 2, and 3 in a H441 xenograft mouse model.

FIG. 12A-G show clinical study of Composition 1 on advanced NSCLC patients. (12A) Progression-free survival, (12B) Overall survival, (12C) Overall survival in lung adenocarcinoma, (12D) Overall survival in lung Non-adenocarcinoma, (12E) lung adenocarcinoma EGFR wild type overall survival, (12F) lung adenocarcinoma with EGFR Mutation overall survival, and (12G) After first-line therapy survival (after RECIST-PD survival).

FIG. 17 shows exemplary Study Protocols (1) and (2).

DETAILED DESCRIPTION OF THE INVENTION

Figure 1C:
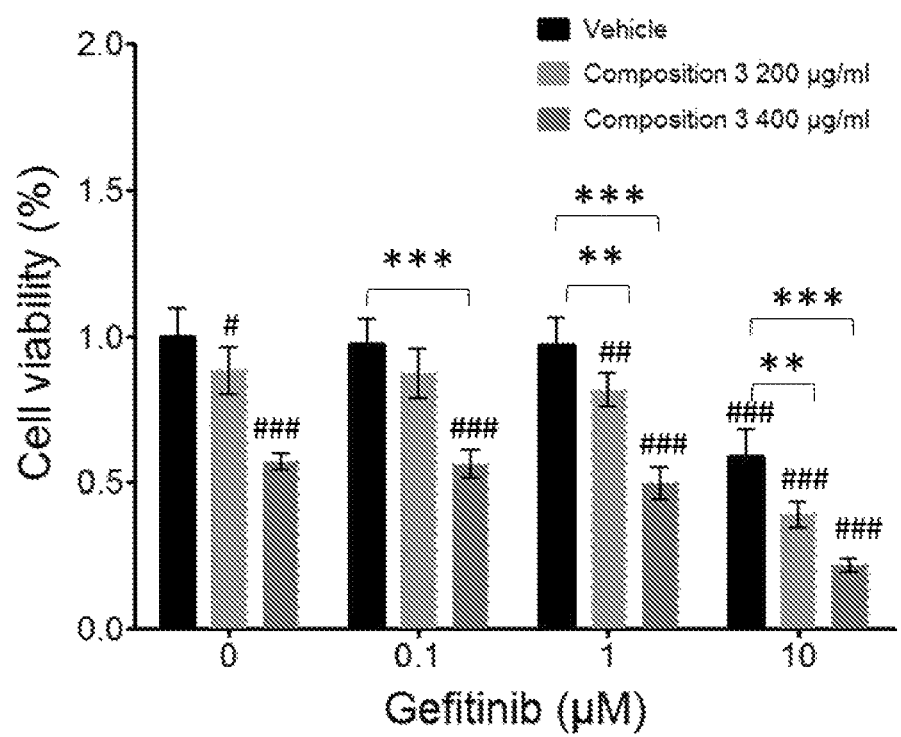

Non-small-cell lung carcinoma (NSCLC) is any type of epithelial lung cancer other than small cell lung carcinoma (SCLC). The most common types of NSCLC are squamous cell carcinoma, large cell carcinoma, and adenocarcinoma, but there are several other types that occur less frequently, and all types can occur in unusual histologic variants and as mixed cell-type combinations. Sometimes the phrase "non-small-cell lung cancer" ("not otherwise specified", or NOS) is used generically, usually when a more specific diagnosis cannot be made. This is most often the case when a pathologist examines a small amount of malignant cells or tissue in a cytology or biopsy specimen. Depending on the stage of the disease and other factors, the main treatment options for people with non-small cell lung cancer (NSCLC) can include: surgery, radiofrequency ablation, radiation therapy, chemotherapy, targeted therapies.

In accordance with the present practice, the treatment of NSCLC, in some embodiments, is for the treatment of any type of epithelial lung cancer other than small cell lung carcinoma (SCLC). In some embodiments, the treatment of NSCLC is for the treatment of squamous cell carcinoma, or large cell carcinoma, or adenocarcinoma, or any types that occur less frequently, and in unusual histologic variants and as mixed cell-type combinations as recognized by any skilled person in the art.

Because of NSCLC's relatively insensitive to chemotherapy, more than one kind of treatment is often used, depending on the stage of the cancer, the individual's overall health, age, response to chemotherapy, and other factors such as the likely side effects of the treatment.

Recently, attention has been paid to Traditional Chinese Medicines (TCM), especially their potential to treat cancer. The principle to apply TCM is based on the practice of the traditional Chinese medicine theory.

For example, based on traditional Chinese medicine theory, in general, disease is perceived as a disharmony (or imbalance) in the functions or interactions of yin, yang, qi, xuĕ (blood), zàng-fŭ (inner organ), meridians etc. and/or of the interaction between the human body and the environment. Therapy is based on which "pattern of disharmony" can be identified. It is known that there are six excesses related to disease models and the treatment thereof. The Six Excesses (sometimes also refer to "Pathogenic Factors" or "Six Pernicious Influences") are allegorical terms used to describe disharmony patterns displaying certain typical symptoms.

The Six Excesses and their characteristic clinical signs are: 1. Wind: rapid onset of symptoms, wandering location of symptoms, itching, nasal congestion, "floating" pulse, tremor, paralysis, convulsion; 2. Cold: cold sensations, aversion to cold, relief of symptoms by warmth, watery/clear excreta, severe pain, abdominal pain, contracture/hypertonicity of muscles, (slimy) white tongue fur, "deep"/"hidden" or "string-like" pulse, or slow pulse; 3. Fire/Heat: aversion to heat, high fever, thirst, concentrated urine, red face, red tongue, yellow tongue fur, rapid pulse; 4. Dampness: sensation of heaviness, sensation of fullness, symptoms of Spleen dysfunction, greasy tongue fur, "slippery" pulse; 5. Dryness: dry cough, dry mouth, dry throat, dry lips, nosebleeds, dry skin, dry stools; and 6. Summerheat: either heat or mixed damp-heat symptoms. Based on the Six Excesses, a doctor may prescribe a Chinese herbal composition to treat a disease diagnosed with one of more of the Excesses. Thus, in general, Chinese medicine may involve more than one herbal medicine to treat diseases.

As such, in some instances, traditional Chinese medicines comprise many components, usually extract of raw natural occurred material with each presents in very small quantity. From the Western medicine point of view, the advantage of this multiple component medicine is to have fewer side effects when any one component is given in large quantity. The approach with multiple component ingredients may be analogous to metronomic chemotherapy which has been extensively studied in the past 10 years.

For example, *Astragalus* is used in traditional Chinese medicine for healing and for diabetes.

*Astragalus* (syn. Astragale, Astragale à Feuilles de Réglisse, Astragale Queue-de-Renard, Astragale Réglissier, Astragali, Astragalo, *Astragalus Membranaceus, Astragalus mongholicus*, Astragli Membranceus also known as huáng qi, běi qi or huáng huā huáng qi is a flowering plant in the family Fabaceae. It is one of the 50 fundamental herbs used in traditional Chinese medicine. *Astragalus* has been asserted to be a tonic that can improve the functioning of the lungs, adrenal glands and the gastrointestinal tract, increase metabolism and sweating, promote healing, and reduce fatigue based on traditional Chinese medicinetheory.

Furthermore, the herb *Astragalus membranaceus* (referred to as AM) (Fisch) has been reported to enhance immune recognition of lung cancers through the inhibition of cytokine production from type II T-helper cells (Pellegrini, Berghella et al. 1996, Wei, Sun et al. 2003), and to stimulate macrophage and natural killer cell activity, further potentiating host immune function (Mills, Kincaid et al. 2000).

However, the herb *Astragalus* may not be effective to treat lung cancer, especially NSCLC based on the data disclosed herein. In accordance with the practice of the present invention, there are provided compositions comprising certain herbal mixture to treat non-small cell lung cancer based on the unexpected experimental data disclosed herein.

In some embodiments, there are provided herbal mixtures comprising a component of at least one species from each of the genus *Astragalus, Cimicifuga foetida rhizoma, Ophiopogon radix, Atractylodes lancea rhizoma, Panax ginseng, Atractylodes rhizoma, Massa medicata fermentata, Citrus reticulata-viride, Citrus reticulata, Glycyrrhizae radix, Schisandra fructus, Angelica sinensis radix, Phellodendron cortex, Alisma rhizoma, Pueraria radix, Ziziphus fructus*-Red, and *Zingiber officinale radix*. This particular combination, also known as Qing-Shu-Yi-Qi-Tang under Traditional Chinese Medicines.

There are many known procedures to extract Qing-Shu-Yi-Qi-Tang. For example, hot water extraction of the mixture of these herbal ingredients is traditionally used among Chinese. Alternatively, an alcohol extraction or even organic solvent extraction (such as DMSO) may be used to provide invention herbal mixtures described herein. A skilled person in the art can readily apply other suitable known methods to extract raw materials included in Qing-Shu-Yi-Qi-Tang.

In some embodiments, provided herein are methods for the treatment of NSCLC by administering a composition (i.e., a herbal mixture) comprising a component of at least one species from each of the genus *Astragalus, Cimicifuga foetida, Ophiopogon, Atractylodes lancea rhizoma, Panax ginseng, Atractylodes rhizoma*-White, *Massa medicata fermentata, Citrus reticulata-viride, Citrus reticulata, Glycyrrhizae radix, Schisandra fructus, Angelica sinensis radix, Phellodendron cortex, Alisma rhizoma, Pueraria radix, Ziziphus fructus*, and *Zingiber officinale radix* to a subject (e.g. a human). The compositions provide therapeutic benefit to a subject being treated for NSCLC or its related symptoms (see Examples 1-15).

In some embodiments, provided herein are methods for the treatment of NSCLC by administering a composition (i.e., a herbal mixture) comprising at least 10 components selected from the group consisting of at least one species in each of the genus *Astragalus, Cimicifuga foetida, Ophiopogon, Atractylodes lancea rhizoma, Panax ginseng, Atractylodes rhizoma*-White, *Massa medicata fermentata, Citrus reticulata-viride, Citrus reticulata, Glycyrrhizae radix, Schisandra fructus, Angelica sinensis radix, Phellodendron cortex, Alisma rhizoma*, and *Pueraria radix*, to a subject (e.g. a human). In certain embodiments, the composition comprises at least 11, 12, 13, 14 or 15 components selected from the group consisting of at least one species in each of the genus *Astragalus, Cimicifuga foetida, Ophiopogon, Atractylodes lancea rhizoma, Panax ginseng, Atractylodes rhizoma*-White, *Massa medicata fermentata, Citrus reticulata-viride, Citrus reticulata, Glycyrrhizae radix, Schisandra fructus, Angelica sinensis Radix, Phellodendron cortex, Alisma rhizoma*, and *Pueraria radix*.

In some embodiments, provided herein are compositions useful for the treatment of NSCLC comprising at least 10 components selected from the group consisting of at least one species in each of the genus *Astragalus, Cimicifuga foetida, Ophiopogon, Atractylodes lancea rhizoma, Panax ginseng, Atractylodes rhizoma*-White, *Massa medicata fermentata, Citrus reticulata-viride, Citrus reticulata, Glycyrrhizae radix, Schisandra fructus, Angelica sinensis radix, Phellodendron cortex, Alisma rhizoma*, and *Pueraria radix*. In certain embodiments, the composition comprises at least 11, 12, 13, 14 or 15 components selected from the group consisting of at least one species in each of the genus *Astragalus, Cimicifuga foetida, Ophiopogon, Atractylodes lancea rhizoma, Panax ginseng, Atractylodes rhizoma*-White, *Massa medicata fermentata, Citrus reticulata-viride, Citrus reticulata, Glycyrrhizae radix, Schisandra fructus, Angelica sinensis radix, Phellodendron cortex, Alisma rhizoma*, and *Pueraria radix*.

*Astragalus* (e.g., *Astragalus radix, Astragalus* root) is a large genus of about 3,000 species of herbs and small shrubs, belonging to the legume family Fabaceae and the subfamily Faboideae. Common names include milkvetch (most species), locoweed (in North America, some species) and goat's-thorn (*A. gummifer, A. tragacanthus*). Some pale-flowered vetches are similar in appearance, but vetches are more vine-like.

*Cimicifuga* (bugbane or cohosh) is a genus of between 12-18 species of flowering plants belonging to the family Ranunculaceae, native to temperate regions of the Northern Hemisphere. *Cimicifuga*, especially *Cimicifuga foetida* or *rhizoma Cimicifugae*, is pungent and sweet in flavor, slightly cold in nature and acting on the lung, spleen and stomach channels. In some embodiments, the *Cimicifuga* species is selected from the group consisting of *Cimicifuga foetida* (such as *Cimicifuga foetida rhizoma*), L. var. *intermedia* Regel (*rhizoma Cimicifugae*), *Cimicifuga simplex, Cimicifuga heracleifolia*, Kom, *Cimicifuga dahurica* (Turcz.) Maxim and *Cimicifuga racemosa* (L.) Nutt.

*Ophiopogon japonicas*, or *Ophiopogon tuber japonici*, or Dwarf Lilyturf Tuber (Mondo grass, Fountain plant, monkey grass, Mai Men Dong (Chinese name)); is a species of *Ophiopogon* native to China, Vietnam, India, and Japan. In traditional Chinese medicine *Ophiopogon japonicus* tuber (*Ophiopogon radix*), known as mai men dong, is the cardinal herb for yin deficiency. According to the Chinese Herbal Medicine Materia Medica, the herb is sweet, slightly bitter and slightly cold, enters the heart, lung and stomach channels and nourishes the yin of the stomach, spleen, heart and lungs and clears heat and quiets irritability.

*Atractylodes lancea rhizoma* and *Atractylodes rhizoma*-White. *Atractylodes lancea* Thunb. is a species of *Atractylodes* that grows in central China. *Atractylodes lancea rhizoma* is a Chinese herbal medicine that is believed to act primarily on the digestive system. *Atractylodes rhizoma* or *Atractylodis rhizoma* (Cang zhú), also known as black atractylodes rhizome or *rhizoma Atractylodes*, is a Chinese herbal medicine. It is the dried rhizome of *Atractylodes lancea* (Thunb.) DC., *Atractylodes chinensis* (DC.) Koidz, or certain other local species including *Atractylodes japonica* Koidz. The medicine is distinguished from bái zhú (white atractylodes rhizome or largehead atractylodes rhizome from *Atractylodes macrocephala*), which is typically cultivated, whereas cāng zhú more often tends to be collected from the wild.

Ginseng (ren-shen) is any one of 11 species of slow-growing perennial plants with fleshy roots, belonging to the genus *Panax* of the family Araliaceae. The root is most often available in dried form, either whole or sliced. Ginseng leaf, although not as highly prized, is sometimes also used. Folk medicine attributes various benefits to oral use of American ginseng and Asian ginseng (*P. ginseng*) roots, including roles as an aphrodisiac, stimulant, type II diabetes treatment, or cure for sexual dysfunction in men. Red ginseng (*Panax ginseng*-Red, hong-sam (Chinese), has been peeled, heated through steaming at standard boiling temperatures of 100° C. (212° F.), and then dried or sun-dried. It is frequently marinated in an herbal brew which results in the root becoming extremely brittle.

*Massa medicata fermentata* (*Medicata fermentita fujianensis Massa* or *Massa fermentata* or medicated Leaven) is made with mashed apricot kernels and *artemisia*. The mixture is covered, fermented for a period of one week, cut into small pieces, and then dried in the sun. It can be used raw or after being parched.

*Citrus reticulata-viride* or *Citri reticulatae viride pericarpium* (green tangerine peel) is the dried pericarp of the young or immature fruits of *Citrus reticulata* Blanco and its cultivars.

*Glycyrrhizae radix* (*Glycyrrhiizae radix* et *rhizoma*) also known as licorice root, and Gan Cao, consists of the dried roots and rhizomes of *Glycyrrhiza glabra* L. and its varieties or of *Glycyrrhiza uralensis* Fisch.

Schisandra (*Schisandra chinensis* or *Schisandrae chinensis*) is a deciduous woody vine native to forests of Northern China and the Russian Far East. The plant likes some shade with moist, well-drained soil. Its berries (*Schisandra fructus*) possess all five basic flavors: salty, sweet, sour, pungent (spicy), and bitter thus called Wu Wei Zi in Chinese. Its berries are used in traditional Chinese medicine, where it is considered one of the 50 fundamental herbs. They are most often used in dried form, and boiled to make a tea.

*Angelica sinensis* commonly known as dong quai or "female ginseng" is an herb from the family Apiaceae, indigenous to China. *Angelica sinensis* grows in cool high altitude mountains in China, Japan, and Korea. The yellowish brown root (i.e., *Angelica sinensis radix*) of the plant is harvested in fall and is well-known Chinese medicine used over thousands years Huáng bǎi or huáng bò is one of the fifty fundamental herbs of traditional Chinese medicine. Known also as *Cortex phellodendri* or *Phellodendron cortex*, it is the bark of one of two species of Phellodendron tree: *Phellodendron amurense* or *Phellodendron chinense*. Bark is collected during the fifth solar term (April 4-20) traditionally. It is sun-dried and cut into slices. The bark may be used raw or fried with salt. A variety of methods of water and ethanol extraction and methods such as "semi-bionic extraction" have been investigated to improve yields.

*Alisma rhizoma* (*Alismatis rhizome* or *Alismatis rhizoma*) is the rhizome of the perennial marsh plant *Alisma orientale* (Sam.) *juzepcz*, of the Alismataceae family. It is grown in ditches, damp ground and shallow pond margins in shallow water.

*Pueraria radix* is the root of the perennial Liane *Pueraria lobata* (wild.) Ohwi. or *Pueraria thomsonii* Benth, which belongs to the family of leguminosae.

*Ziziphus jujube* (*Fructus zizyphi jujubae*, or *Jujubae fructus*), commonly called jujube, red date, Chinese date, Korean date, or Indian date is a species of *Ziziphus* in the buckthorn family (Rhamnaceae), used primarily as a shade tree that also bears fruit. The fruit, *Ziziphus fructus*, is particular useful in TCM.

*Zingiber officinale* (or *Rhizoma zingiberis officinalis*, or *Zingiberis officinale* Rosc) is the fresh rhizome and root of perennial herbaceous plant *Zingiber officinale* Rosc of family Zingiberaceae.

In some embodiments provide a composition for treating non-small cell lung cancer in a subject comprising an extract or powder of a herbal mixture, and an anti-cancer agent, wherein said herbal mixture comprises a component of at least one species from each of the genus *Astragalus*, *Cimicifuga foetida rhizoma*, *Ophiopogon radix*, *Atractylodes lancea rhizoma*, *Panax ginseng*-Red, *Atractylodes rhizoma*-White, *Massa medicata fermentata*, *Citrus reticulata-viride*, *Citrus reticulata*, *Glycyrrhiza radix*, *Schisandra fructus*, *Angelica sinensis radix*, *Phellodendron cortex*, *Alisma rhizoma*, *Pueraria radix*, *Ziziphus fructus*-Red, and *Zingiber officinale radix*.

In certain embodiments, the method further comprises administering an anti-cancer agent. The combination therapy is particularly useful for the treatment of NSCLC.

In accordance with the practice of this invention, a herbal mixture comprising a component of at least one species from each of the genus *Astragalus*, *Cimicifuga foetida*, *Ophiopogon*, *Atractylodes lancea*, *Panax ginseng*-Red, *Atractylodes rhizoma*-White, *Massa medicata fermentata*, *Citrus reticulata-viride*, *Citrus reticulata*, *Glycyrrhiza radix*, *Schisandra fructus*, *Angelica sinensis radix*, *Phellodendron cortex*, *Alisma rhizoma*, *Pueraria radix*, *Ziziphus fructus*-Red, and *Zingiber officinale radix* is useful to treat lung cancer (especially NSCLC). Specifically, it was found unexpectedly that the combination of the invention herbal mixture with an anti-cancer agent is particular effective to treat NSCLC.

In some embodiments, there are provided compositions for treating non-small cell lung cancer in a subject comprising an extract or powder of a herbal mixture, and an anti-cancer agent, wherein said herbal mixture comprises a component of at least one species from each of the genus *Astragalus*, *Cimicifuga foetida*, *Ophiopogon radix*, *Atractylodes lancea rhizoma*, *Panax ginseng*-Red, *Atractylodes rhizoma*-White, *Massa medicata fermentata*, *Citrus reticulata-viride*, *Citrus reticulata*, *Glycyrrhiza radix*, *Schisandra fructus*, *Angelica sinensis radix*, *Phellodendron cortex*, *Alisma rhizoma*, *Pueraria radix*, *Ziziphus fructus*, and *Zingiber officinale*.

In certain embodiments, the compositions useful for the treatment of NSCLC comprise at least 10 components selected from the group consisting of at least one species in each of the genus *Astragalus*, *Cimicifuga foetida*, *Ophiopogon*, *Atractylodes lancea rhizoma*, *Panax ginseng*, *Atractylodes rhizoma*-White, *Massa medicata fermentata*, *Citrus reticulata-viride*, *Citrus reticulata*, *Glycyrrhizae radix*, *Schisandra fructus*, *Angelica sinensis radix*, *Phellodendron cortex*, *Alisma rhizoma*, and *Pueraria radix* and an anti-cancer agent. In certain embodiments, the composition comprises at least 11, 12, 13, 14 or 15 components selected from the group consisting of at least one species in each of the genus *Astragalus, Cimicifuga foetida, Ophiopogon, Atractylodes lancea rhizoma, Panax ginseng, Atractylodes rhizoma*-White, *Massa medicata fermentata, Citrus reticulata-viride, Citrus reticulata, Glycyrrhizae radix, Schisandra fructus, Angelica sinensis radix, Phellodendron cortex, Alisma rhizoma,* and *Pueraria radix* and an anti-cancer agent.

In some embodiments, examples of anti-cancer agents are found in *Cancer Principles and Practice of Oncology* by V. T. Devita and S. Hellman (editors), 6$^{th}$ edition (Feb. 15, 2001), Lippincott Williams & Wilkins Publishers. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, PPAR agonists, inhibitors of inherent multidrug resistance (MDR), antiemetic agents, agents useful in the treatment of anemia, agents useful in the treatment of neutropenia, immunologic-enhancing drugs, biphosphonates, aromatase inhibitors, agents inducing terminal differentiation of neoplastic cells, γ-secretase inhibitors, cancer vaccines, and any combination thereof.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpr-opanoate, 4,4'-dihydroxybenzophenone-2,4-dinitrophenyl-hydrazone, and SH646.

In some embodiments, estrogen receptor modulators are tamoxifen and raloxifene.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mitosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)-benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',':6,7)colchic(2,3-d)-1,3-dioxol-6-one, 2,3-(methylenedioxy)-5-methyl-7-hydroxy-8-methoxybenzo[c]-phenanthridinium, 6,9-bis[(2-aminoethyl)-amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2-,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydrobenzofuryl)sulfonyl]-N'-(3,4-dichlorophenyl)urea, N6-[4-deoxy-4-[N$^2$-[2(E),4(E)-tetradecadienoyl]-glycylamino]-L-glycero-B-L-manno-heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 1'-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which in some embodiments are delivered via recombinant virus-mediated gene transfer.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chloropheny-1)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethyl-phenyl)-4-[1-(4-cyanobenzyl)-5-imidazolylmethyl]-2-piperazinone, (5)-1-(3-chlorophenyl)-4-[1-(4-cyanobenzyl)-5-imidazolylmethyl]-542-(ethanesulfonyl)-methyl]-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-yl-ethyl)carbamoyl]-piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2]bipyridin-5'-ylmethyl]-3H-imidazol-4-ylmethyl}benzonitrile, 4-{3-[4-(2-oxo-2H-[1,2]bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl]benzonitrile, 18,19-dihydro-19-oxo-5H,17H-6,10:12,16-dimetheno-1H-imidazo[4,3-c][1,11,4]dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]-oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacyclo-eicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

"HMG-CoA reductase inhibitors" refers to inhibitors of 3-hydroxy-3-methylglutaryl-CoA reductase. In some embodiments, compounds which have inhibitory activity for HMG-CoA reductase are readily identified by using known assays. The terms "HMG-CoA reductase inhibitor" and "inhibitor of HMG-CoA reductase" have the same meaning when used herein.

In some embodiments, examples of HMG-CoA reductase inhibitors that are used include but are not limited to lovastatin (MEVACOR®), simvastatin (ZOCOR®), pravastatin (PRAVACHOL®), fluvastatin (LESCOL®), atorvastatin (LIPITOR®) and cerivastatin (also known as rivastatin and BAYCHOL®). In some embodiments, the structural formulas of these and additional HMG-CoA reductase inhibitors that are used in the instant methods are described at page 87 of M. Yalpani, "Cholesterol Lowering Drugs", Chemistry & Industry, pp. 85-89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is intended to be covered.

In some embodiments, in HMG-CoA reductase inhibitors where an open-acid form exists, salt and ester forms are formed from the open-acid, and all such forms are included within the meaning of the term "HMG-CoA reductase inhibitor" as used herein. In some embodiments, the HMG-CoA reductase inhibitor is selected from lovastatin and simvastatin. In one embodiment, the HMG-CoA reductase inhibitor is simvastatin.

Herein, the term "pharmaceutically acceptable salts" with respect to the HMG-CoA reductase inhibitor shall mean non-toxic salts of the compounds employed which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. In other embodiments, further examples of salt forms of HMG-CoA reductase inhibitors include, but are not limited to, acetate, benzenesulfonate, benzoate, bicarbonate, bisulfate, bitartrate, borate, bromide, calcium hydroxyl, camsylate, carbonate, chloride, clavulanate, citrate, dihydrochloride, hydroxyl, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

In other embodiments, ester derivatives of the described HMG-CoA reductase inhibitor compounds act as prodrugs which, when absorbed into the bloodstream of a warm-blooded animal, cleave in such a manner as to release the drug form and permit the drug to afford improved therapeutic efficacy.

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HB Y097, lamivudine, nevirapine, AZT, 3TC, ddC, and ddI. It has been reported that HIV protease inhibitors, such as indinavir or saquinavir, have potent anti-angiogenic activities and promote regression of Kaposi sarcoma.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1)

and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib, carboxyamidotriazole, combretastatin A-4, squalamine, 6-O-chloroacetyl-carbonyl)-fumagillol, thalidomide, angiostatin, troponin-1, angiotensin II antagonists, and antibodies to VEGF.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RP14610, NX31838, sulfated mannopentose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

"Inhibitors of cell proliferation and survival signaling pathway" refer to pharmaceutical agents that inhibit cell surface receptors and signal transduction cascades downstream of those surface receptors. Such agents include inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PDK or PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include, but are not limited to, activators of TNF receptor family members (including the TRAIL receptors).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include, but not limited to, tyrosine kinase inhibitors such as inhibitors of c-Kit, Eph, PDGF, Flt3 and c-Met. Further agents include inhibitors of RTKs. Examples of "tyrosine kinase inhibitors" include, but not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]-quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2', 1'-kl]pyrrolo[3,4-i][1,6]benz odiazocin-1-one, SH268, genistein, ST1571, CEP2563, 4-(3-chlorophenylamino)-5,6-dimethy-7-1H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, SU11248, STI571A, N-4-chlorophenyl-4-(4-pyridylmethyl)-1-phthalazinamine, and EMD121974.

As used above, "integrin blockers" refers to compounds which selectively antagonize, inhibit or counteract binding of a physiological ligand to the $α_vβ_3$ integrin, to compounds which selectively antagonize, inhibit or counter-act binding of a physiological ligand to the $α_vβ_5$ integrin, to compounds which antagonize, inhibit or counteract binding of a physiological ligand to both the $α_vβ_3$ integrin and the $α_vβ_5$ integrin, and to compounds which antagonize, inhibit or counteract the activity of the particular integrin(s) expressed on capillary endothelial cells. The term also refers to antagonists of the $α_vβ_6$; $α_vβ_8$, $α_2β_1$, $α_5β_1$, $α_6β_1$ and $α_6β_4$ integrins. The term also refers to antagonists of any combination of a $α_vβ_3$, $α_vβ_5$, $α_vβ_6$, $α_vβ_8$, $α_1β_1$, $α_2β_1$, $α_5β_1$, $α_6β_1$ and $α_6β_4$ integrins.

"Tyrosine kinase inhibitor (TKI)" refers to a pharmaceutical drug that inhibits tyrosine kinases. They are also called tyrphostins, the short name for "tyrosine phosphorylation-inhibitor" which was the first description of compounds inhibiting the catalytic activity of the epidermal growth factor receptor (EGFR). Thus tyrosine kinase inhibitors also refer to all EGFR tyrosine kinase inhibitors or EGFR inhibitors. In some embodiments, compounds which have inhibitory activity for tyrosine kinases are readily identified by using known assays.

In some embodiments, examples of tyrosine kinase inhibitors that are used include but are not limited to afatinib, erlotinib, osimertinib (AZD9291), AZD3759, gefitinib, canertinib, lapatinib, cetuximab, matuzumab, zalutumumab, and panitumumab, or a pharmaceutically acceptable salt thereof. In some embodiments, tyrosine kinase inhibitors comprise afatinib, erlotinib, osimertinib (AZD9291), AZD3759, or gefitinib.

Exemplary classes of anticancer agents suitable for use in compositions and methods of the present invention include, but are not limited to: 1) alkaloids, such as microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, comprising topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.), and the like; 2) covalent DNA-binding agents (alkylating agents), such as nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents (antitumor antibiotics), such as nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), and the like; 4) antimetabolites, such as antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.), and the like; 5) enzymes with anticancer effect, such as L-asparaginase; 6) hormones that inhibit cancer growth, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-α, etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

In some embodiments, the anti-cancer agents are alkaloids, alkylating agents, antibumor antibiotics, antimetabolites, enzymes with anticancer effect, hormones that inhibit cancer growth, platinum compounds, monoclonal antibodies conjugated with anticancer drugs, biological response modifiers (e.g., interferons [e.g., IFN-α, etc.] and interleukins, agents that induce tumor cell differentiation, or inhibitors of angiogenesis.

In some embodiments, the anti-cancer agent is selected from the group consisting of estrogen receptor modulators, androgen receptor modulators, retinoid receptor modulators, cytotoxic/cytostatic agents, antiproliferative agents, prenyl-protein transferase inhibitors, HMG-CoA reductase inhibitors, nitrogen mustards, nitroso ureas, angiogenesis inhibitors, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, PPAR agonists, inhibitors of inherent multidrug resistance (MDR), anti-emetic agents, agents useful in the treatment of anemia, agents useful in the treatment of neutropenia, immunologic-enhancing drugs, biphosphonates, aromatase inhibitors, agents inducing terminal differentiation of neoplastic cells, γ-secretase inhibitors, and cancer vaccines. In certain embodiments, the anti-cancer agent is selected from the group consisting of gemcitabine, idarubicin/cytarabine, etopside phosphate, gleevac, temozolomide, bortezomib, letrozole, cetuximab, bevacizumab, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, lpilimumab, RAD001, Pazopanib, FOLFIRI, BKM120, GSK1120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifarnib/gemcitabline, tootecan, or combinations thereof. In certain embodiments, the anti-cancer agent is cisplatin.

In some embodiments, the agent that interfere with receptor tyrosine kinases (RTKs) (i.e., EGFR inhibitor) is selected from the group consisting of afatinib, erlotinib, osimertinib (AZD9291), AZD3759, gefitinib. In certain embodiments, the EGFR inhibitor is gefitinib.

In some embodiments, the anti-cancer agent is a cytotoxic agent. In certain embodiments, the cytotoxic agent is selected from the group consisting of afatinib, erlotinib, osimertinib (AZD9291), AZD3759, gefitinib, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin. In certain embodiments, the anti-cancer agent is cisplatin or gefitinib.

The herbal mixture compositions were further studied to realize their potential to treat lung cancer, especially NSCLC. In accordance with the practice of the invention, the invention compositions provide useful clinical benefit with or without an anti-cancer agent.

In some embodiments, the invention compositions improve the efficacy of cisplatin-based chemotherapy. In some embodiments, the invention compositions described herein increase the production of IL-1 β expression. In certain embodiments, the compositions described herein increase the production of TNF-α expression. In certain embodiments, the compositions described herein inhibit angiogenesis, or ABCG2. In certain embodiments, the compositions reduce phosphor-EGFR mediated signaling or prevent lipolysis, or overcome gefitinib resistance.

In some embodiments provide a method for treating non-small cell lung cancer in a subject comprising administering an extract or powder of a herbal mixture, optionally with an anti-cancer agent to said subject wherein said herbal mixture comprises a component of at least one species from each of the genus *Astragalus, Cimicifuga foetida rhizoma, Ophiopogon radix, Atractylodes lancea rhizoma, Panax ginseng*-Red, *Atractylodes rhizoma*-White, *Massa medicata fermentata, Citrus reticulata-viride, Citrus reticulata, Glycyrrhiza radix, Schisandra fructus, Angelica sinensis radix, Phellodendron cortex, Alisma rhizoma, Pueraria radix, Ziziphus fructus*-Red, and *Zingiber officinale radix*. In certain embodiments, the non-small cell lung cancer is adenocarcinomas, or large cell carcinomas. In certain embodiments, said method decreases non-small cell lung cancer tumor growth rate. In certain embodiments, said method reduces non-small cell lung cancer tumor size or tumor volume. In certain embodiments, the optional anti-cancer agent is is selected from the group consisting of afatinib, erlotinib, osimertinib (AZD9291), AZD3759, gefitinib, gemcitabine, idarubicin/cytarabine, etopside phosphate, gleevac, temozolomide, bortezomib, letrozole, cetuximab, bevacizumab, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, lpilimumab, RAD001, Pazopanib, FOLFIRI, BKM120, GSKI120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifamib/ gemcitabline, topotecan, or combinations thereof. In certain embodiments, the anti-cancer agent is cisplatin or gefitinib.

In some embodiments, said extract or powder of herbal mixture, and said optional anti-cancer agent is administered separately, simultaneously or sequentially. In some embodiments, said extract or powder of herbal mixture, and said optional anti-cancer agent are administered orally, parenterally intravenously or by injection.

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "combination" as used herein, means a product that results from the mixing or combining of more than one active ingredient and includes both fixed and non-fixed combinations of the active ingredients. The term "fixed combination" means that the active ingredients, e.g. a herbal mixture (e.g., invention Composition 1, or the like described herein) and a co-agent, are both administered to a patient simultaneously in the form of a single entity or dosage. The term "non-fixed combination" means that the active ingredients, e.g. a herbal mixture (e.g., invention Composition 1, or the like described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration and Dosage

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, an anti-cancer agent is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, an anti-cancer agent is administered parenterally or intravenously. In other embodiments, an anti-cancer agent is administered by injection. In some embodiments, an anti-cancer agent is administered orally.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

General Consideration for Combination Treatments

In general, the compositions described herein and, in embodiments where combinational therapy is employed based on the mode of action described herein, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

EXAMPLES

Example 1. Herbal Materials and Preparation of Herbal Mixture Extracts

The decoction of Composition 1 used in this study was prepared as lyophilized powder of water extraction from the following ingredients: *Astragalus radix* (Huang Qi) 12.50%, *Cimicifuga foetida rhizoma* (Sheng Ma) 12.50%, *Ophiopogon radix* (Mai Men Dong) 8.33%, *Atractylodes lancea rhizoma* (Cang Zhu) 8.33%, *Panax ginseng*-Red (Ren Shen) 6.25%, *Atractylodes rhizoma*-White (Bai Zhu) 6.25%, *Massa medicata fermentata* (Shen Qu) 4.17%, *Citrus reticulata-viride* (Qing Pi) 4.17%, *Citrus reticulata* (Chen Pi) 4.17%, *Glycyrrhizae radix* (Gan Cao) 4.17%, *Schisandra fructus* (Wu Wei Zi) 4.17%, *Angelica sinensis radix* (Dang Gui) 4.17%, *Phellodendron cortex* (Huang Bai) 4.17%, *Alisma rhizoma* (Ze Xie) 4.17%, *Pueraria radix* (Ge Gen) 4.16%, *Ziziphus fructus*-Red (Da Zao) 4.16%, and *Zingiber officinale radix* (Sheng Jiang) 4.16%. Composition 1 has been used as a Chinese medicine to clear summer heat, augment the qi, nourish the yin, and generate fluids.

The decoction of *Astragalus membranaceus* and Qing-Shu-Yi-Qi-Tang were dissolved in water (referred to as AM-Decoction-H$_2$O and Composition 1, respectively) or dimethyl sulfoxide (referred to as AM-Decoction-DMSO and Composition 4, respectively). They were prepared by vortex 1 minute and sat for 5 minutes (3 cycles), centrifuged immediately for 10 minutes (4000 rpm, twice) and filtered through a 0.45 um filter (Millipore) to obtain the supernatant. In some instances, the powdered concentrated herbal extracts Qing-Shu-Yi-Qi-Tang and Qing-Shu-Yi-Qi-Tang decoction were extracted by ethanol (referred to as Composition 3 and Composition 5, respectively) or water (referred to as Composition 2). For aqueous and ethanol extraction, the ingredients per gram were dissolved in 10 mL water or 95% ethanol (for one hours), followed by gentle removal of solvents by rotary evaporator. All compositions were aliquoted and stored at −20° C. as stock solution for experiments.

In comparison to *Astragalus* only to enhance immune recognition of lung cancers, the following compositions were prepared.

TABLE 1

Compositions of various Invention Compositions

| Ingredients and methods | Extraction | Dissolved solvent | Sample |
|---|---|---|---|
| Aqueous extract of *Astragalus membranaceus* decoction | $H_2O$ | $H_2O$ | AM-Decoction-$H_2O$ |
| *Astragalus membranaceus* decoction | None | DMSO | AM-Decoction-DMSO |
| Qing-Shu-Yi-Qi-Tang | None | $H_2O$ | Composition 1 |
| Aqueous extract of Qing-Shu-Yi-Qi-Tang | $H_2O$ | $H_2O$ | Composition 2 |
| Ethanol extract of Qing-Shu-Yi-Qi-Tang | EtOH | DMSO | Composition 3 |
| Qing-Shu-Yi-Qi-Tang Decoction | None | DMSO | Composition 4 |
| Ethanol extract of Qing-Shu-Yi-Qi-Tang Decoction | EtOH | DMSO | Composition 5 |

Example 2. Cell Lines and Cell Culture Preparation

All the lung cancer cell lines were maintained in RPMI supplemented with 10% fetal calf serum (FBS, Invitrogen) and 2 mM L-glutamine (Invitrogen), 1% penicillin/Streptomycin/Amphotericin B Solution, 1% NEAA (Nonessential amino acids) at 37° C. in 5% $CO_2$.

Example 3: Cancer Cell Survival Study of Composition 2, Composition 3 in Comparison with AM-Decoction-DMSO Cell Viability Assays In this study, various cell lines such as lung adenocarcinoma cancer cells, A549, CL141, and CL97 (harboring EGFR-G719A-T790M mutations), H441, H23, HCC827, PC-9, H1650, H1975, lung squamous cancer cells, CL152, H226, H1299, and large cell lung carcinoma, H460 were treated with a wide range of 25, 50, 100, 200, 400 μg/ml of AM-Decoction-DMSO, Composition 2 and Composition 3 for 10 days. The colony is defined to consist of at least 50 cells. Colonies were fixed with a mixture of methanol and acetic acid (3:1) and stained with 0.5% crystal violet. The $IC_{50}$ values of Composition 3 were lower than Composition 2 at all cell lines. Therefore, Composition 3 could effectively inhibit the colony formation (Table 2, left). Moreover, to investigate the cytotoxicity of Composition 2 and Composition 3, various cells were treated with Composition 2 and Composition 3 for 24, 48 and 72 hours, followed by sulforhodamine B colorimetric (SRB) assay. The data showed that Composition 3 reduces the cell viability of A549 (the IC50 values was about 294±43 μg/ml) about 50% in 72 hours (Table 2, right). Together, both Composition 2 and Composition 3 reduced the colony formation ability in different lung cancer cells. Composition 3 had low cytotoxicity in SRB assay, but had significant ability of suppression in colony formation with lower concentration. In vitro data indicates that Composition 3 may be a more superior anti-lung cancer cell agent than Composition 2.

TABLE 2

Summary of cytotoxicity and clonogenic results of Composition 2, Composition 3 and AM-decoction-DMSO in various lung cancer cell lines

| | Clonogenic Assay | | | SRB Assay | |
|---|---|---|---|---|---|
| Cell line | $IC_{50}$ of AM-Decoction-DMSO (μg/mL) | $IC_{50}$ of Composition 2 (μg/mL) | $IC_{50}$ of Composition 3 (μg/mL) | $IC_{50}$ of Composition 2 (μg/mL) for 72 hours | $IC_{50}$ of Composition 3 (μg/mL) for 72 hours |
| A549 | >400 | >400 | 155 ± 16 | >400 | 294-143 |
| CL141 | ND | >400 | 258 ± 50 | >400 | >400 |
| NCI-H441 | ND | >400 | 171 ± 22 | >400 | >400 |
| NCI-H23 | ND | >400 | 197 ± 33 | >400 | >400 |
| HCC827 | ND | >400 | 247 ± 17 | >400 | >400 |
| PC-9 | ND | 295 ± 30 | 142 ± 36 | >400 | >400 |
| NCI-H1650 | ND | ND | ND | >400 | >400 |
| CL97 | ND | >400 | 168 ± 15 | >400 | >400 |
| NCI-H1975 | ND | 316 ± 14 | 158 ± 15 | >400 | >400 |
| CL152 | ND | 195 + 15 | 175 ± 10 | >400 | >400 |
| NCI-H226 | ND | 272 ± 34 | 171 ± 16 | >400 | >400 |
| NCI-H1299 | >400 | ND | ND | ND | ND |
| NCI-H460 | ND | >400 | 195 + 45 | >400 | >400 |

Example 4. Combination Therapy Studies of Invention Compositions with Cisplatin or Gefitinib The cytotoxicity of the combination treatment of cisplatin or gefitinib (a tyrosine-kinase inhibitor) with Composition 3 in lung cancer cells was studied. Cells were seeded in 96 well plates for 1 day. Tested drugs were added 24 hours after seeding of the cells and incubated for 48 or 72 hours. The number of viable cells was estimated using the Sulforhodamine Bassay (SRB assay). Cells were fixing with 10% trichloroacetic acid (TCA) for 1 hour. TCA was then removed and stained with sulforhodamine B(SRB) for 1 hour. After rinsing the plates with 1% acetic acid, 20 mM Tris base solution was added to each well to solubilize the protein-bound dye, followed by the color intensity measurement at 540 nm in a microplate reader. The DMSO or corresponding vehicle treated cells were considered to be control and assigned a value of 100%.

Figure 2:
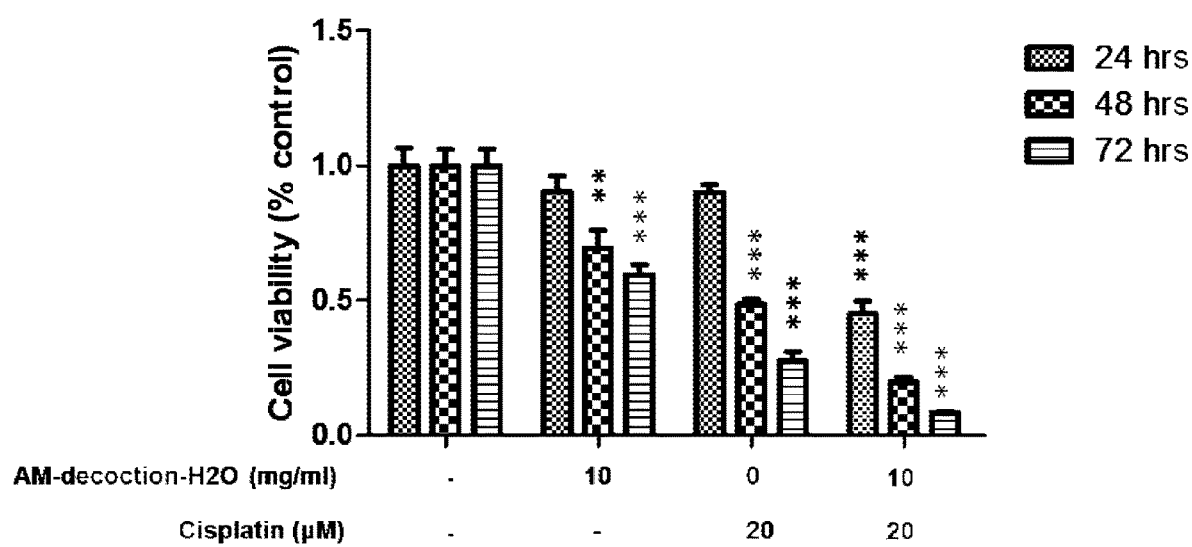
FIG. 2 shows illustrative results of cell line cytotoxicity study of AM-Decoction-$H_2O$ (i.e., water extracts of *Astragalus*) with cisplatin on lung cancer A549 cells. A10: AM-Decoction-$H_2O$ (10 mg/L), C20: Cisplatin (20 μM), (t-test, *: p value<0.05; : p value<0.01; *: p value<0.001 compared different treatments with vehicle control.).

The cell survival rate for combination treatment of cisplatin or gefitinib with Composition 3 showed that drug combination increased the cytotoxicity of cisplatin or gefitinib as compared with cisplatin or gefitinib only (FIG. 1A-C). As the result of statistics analysis, high concentration of gefitinib or/and Composition 3 showed cytotoxicity on lung cancer cells (label with pound sign). And the cytotoxicity of drug combination on lung cancer cells significantly increase compared with one drug alone (label with asterisk). Interestingly, when AM was dissolved with $H_2O$, AM-Decoction-$H_2O$ had synergistic effect with cisplatin (FIG. 2).

Figure 3B:
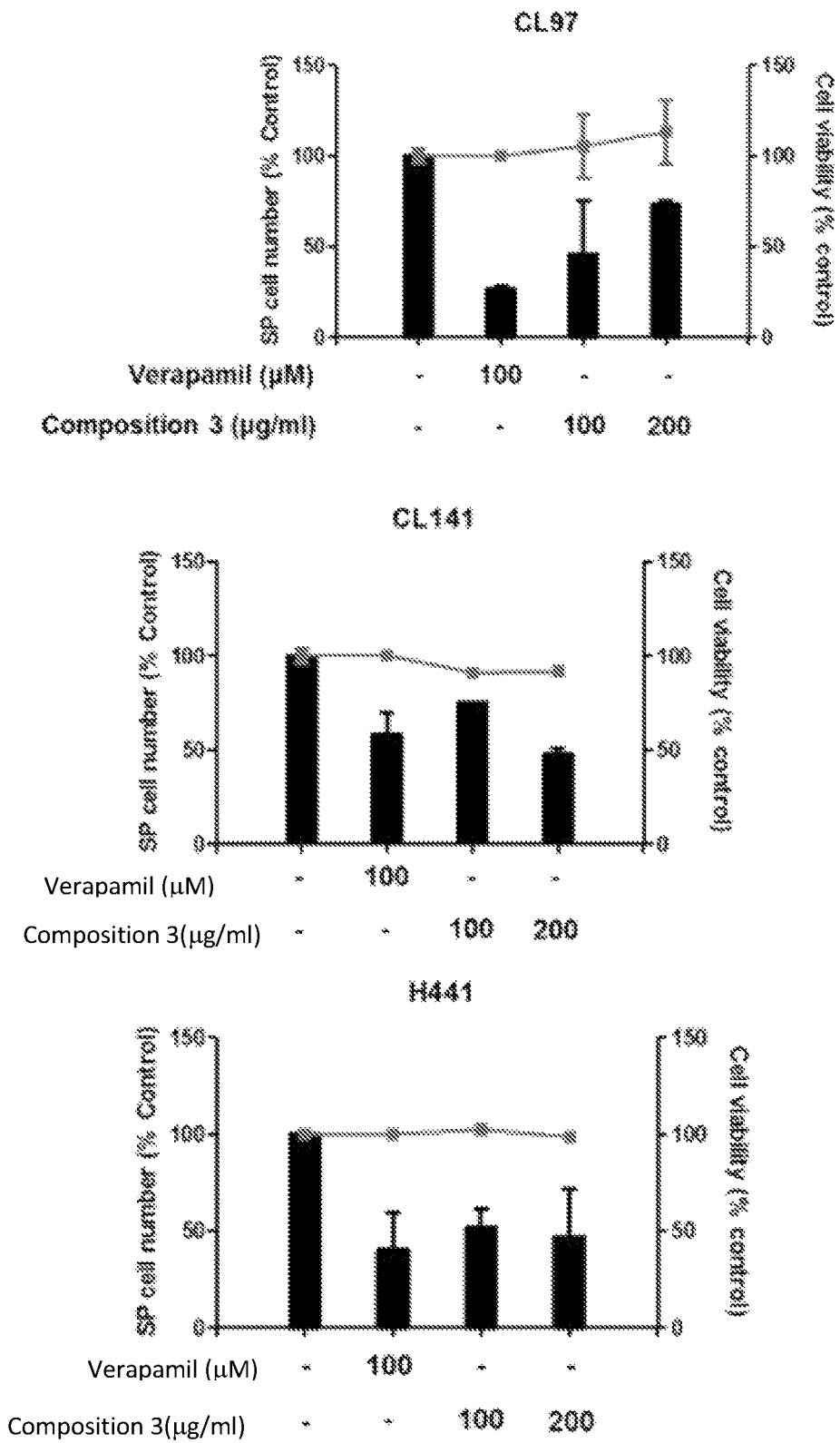

Next, the isolation of CSCs using side-population method via flow cytometry of the corresponding cell lines A549, CL141, and H441 was conducted with AM-Decoction-$H_2O$, AM-Decoction-DMSO, Compositions 3, 4, and 5. The side population cells of CL141 (FIG. 3A) were gated after AM-Decoction-$H_2O$, AM-Decoction-DMSO, Composition 4, and Composition 5 treatment for 48 hr. The cancer stem-like side population was significantly decreased by AM-Decoction-$H_2O$, AM-Decoction-DMSO, Composition 4, and Composition 5. As shown in FIG. 3B, Composition 3 can decrease the side population of lung cancer cell lines, including CL97, CL141, and H441.

Example 5: Colony Formation Inhibition Study in Non-Small Cell Lung Carcinomas by Composition 3

Cells were seeded in 6 well plates with 800 cells per well for 14 days. Tested drugs were added 24 hours after seeding of the cells. The medium and drugs were changed every 4 days. After the treatments, cells were washed with PBS, and the colonies were fixed with fix solution (methanol: acetic acid=3:1) and stained with 0.5% crystal violet in methanol. After removing the crystal violet carefully and rinse with tap water, the colonies were counted manually. Each experiment was performed independently at least triplicate and cytotoxicities are given as means±SD.

Clonogenic assay was used to test the inhibition ability of forming colonies in A549 cells (FIG. 4A) from five different brands (brand A-brand E) of Composition 3 (200 µg/ml) and BZ-EtOH (200 µg/ml) (FIG. 4B), which is another Chinese herbal medicine (Bun-Zong-Yi-Qi-Tang) with similar 9 ingredients to Composition 1 as a negative control. BZ has 8 ingredients same as Composition 1 (which are *Astragalus, Cimicifuga foetida rhizoma, Panax ginseng*-Red, *Atractylodes rhizoma*-White, *Citrus reticulata, Glycyrrhiza radix, Angelica sinensis radix, Ziziphus fructus*, and *Zingiber officinale radix*) and one ingredient different (which is *Bupleurum chinense*).

In addition, A549 cells were treated with different dosages of Composition 3, which was from the specific brand used in this study (FIG. 4C), and with five additional batches (batch A-batch E) of Composition 3 (200 µg/ml) from the same brand, followed by clonogenic assay (FIG. 4D). Control cells were treated with solvent (DMSO) and colonies were used as 100%. One colony is defined to consist of at least 50 cells. (t test, *: p value<0.05; : p value<0.01;*: p value<0.001).

The data showed that all different brands (i.e., batches) of Composition 1, but not BZ, had some degree of anti-colony formation ability.

Example 6: Cancer Stem-Like Cell Survival Study by Composition 3

Cells were seeded in 6 cm dish with $5 \times 10^5$ cells per dish for 1 day. Tested drugs were added 24 hours after seeding of the cells and incubated for 48 hours. Single-cell suspensions of cells were detached from dishes with Trypsin-EDTA (Invitrogen) and suspended at $1 \times 10^6$ cells/mL in Hank's balanced salt solution (HBSS) supplemented with 3% fetal calf serum and 10 mM Hepes. These cells were then incubated at 37° C. for 90 minutes with 20 µg/mL Hoechst 33342 (Sigma Chemical, St. Louis, Mo.), either alone or in the presence of 50 µmol/L verapamil (Sigma), an inhibitor of the verapamil-sensitive ABC transporter. After 90 minutes incubation, the cells were centrifuged immediately for 5 minutes at 300 g and 4° C. and resuspended in ice-cold HBSS. The cells were kept on ice to inhibit efflux of the Hoechst dye, and 1 µg/mL propidium iodide (BD) was added to discriminate dead cells. Finally, these cells were filtered through a 40 µm cell strainer (BD) to obtain single-suspension cells. Cell dual-wavelength analysis and purification were performed on a dual-laser FACS Vantage SE (BD). Hoechst 33342 was excited at 355 nm UV light and emitted blue fluorescence with a 450/20 band-pass (BP) filter and red fluorescence with a 675 nm edge filter long-pass (EFLP). A 610 nm dichroic mirror short-pass (DMSP) was used to separate the emission wavelengths. PI-positive (dead) cells were excluded from the analysis.

To culture cancer stem-like cell and compare their characteristic with parental cancer cells. CL141 and CL97 tumor spheres showing up-regulation of lung cancer stem cell markers CD133 and CD44 were generated for evaluating efficacy of Composition 3 (see FIG. 5A-B). In cancer stem-like cell cytotoxicity test showed that Composition 3 has significant cytotoxicity on cancer stem-like cell, but not on parental cells (see FIG. 5C-D).

FIG. 5A shows results of cell morphology of parental CL97 and CL141 cells and anchorage independent culture of CL97 and CL141 sphere cells. The results of using western blot to examine the expression of sternness markers in CL97 and CL141 parental and sphere cells are shown in FIG. 5B. CL97 and CL141 secondary sphere cells were treated with different concentrations of Composition 3 for 48 hrs and the survival cells were counted as shown in FIGS. 5C and 5D (control cells were treated with DMSO and used as 100%). (t-test, *: p value<0.05; : p value<0.01;*: p value<0.001). Composition 3 significantly reduced the viability of stem-like sphere cells, but not in lung cancer cells.

Example 7: Studies of Sternness Markers and Wnt Target Expression by Composition 3

EZH2 (enhancer of zeste homologue 2), a critical gene which is known to regulate cell cycle, DNA repair, and cell differentiation. EZH2 also has been reported to associate with several types of cancer stem cell. Studies of sternness markers and Wnt target expression by Composition 3 were conducted.

CL97 and CL141 spheres were seeding in 25T flask. Parental cells, CL97 and CL141 were seeding in cultured dish. After 48 hours of non-treatment, harvested cells were subject to western blot analysis. Samples were run on 10% Tris-Glycine gel and subjected to SDS polyacrylamide gel electrophoresis and electrotransferred onto PVDF membranes (Millipore). Primary antibody was from cell signaling, and second antibody for anti-rabbit horseradish peroxidase (HRP)-conjugation was from GeneTex. The protein detection was performed with enhanced chemiluminescence (ECL™) method captured by a Luminescence Imaging System (LAS-4000™, Fuji Photo Film Co., Ltd).

Study results are shown in FIGS. 6A-C. After treating with Composition 3, EZH2 was down-regulated in CL97 and CL141 sphere cells, respectively as shown in FIG. 6A. According to FIG. 6B results, Composition 3 can significant reduce sternness marker, Oct4, in A549-ON, which is a stable clone with overexpression of Oct4 and Nanog. Based on FIG. 6C, Composition 3 can significant reduce lung cancer cell sternness markers (such as CD133, Oct4 and Sox2) and Wnt targets (beta-catenin and p-GSK3β) in a dose-dependent manner in CL141 spheres.

Example 8: ABCG2 Transport Activity Inhibition Study with Compositions 2 and 3

The activities of Composition 3 and Composition 2 on ATP-binding cassette subfamily G member 2, ABCG2 (also known as the breast cancer resistance protein, BCRP), which is a plasma membrane drug efflux pump that is associated with multi-drug resistance phenotype and as the side population marker for identifying CSCs in lung cancers were examined. It was found that Composition 3, but not Composition 2, can moderately inhibit the transport activity of ABCG2 in R482-HEK293 cells (HEK293 cells stably transfected with wild-type human ABCG2 protein). Ko143 is a benchmark inhibitor of ABCG2, and was used here as positive control (FIGS. 7A/B).

The accumulation of fluorescent pheophorbide-A (PhA) in drug-sensitive parental HEK293 cells or ABCG2-transfected HEK293 cells (referred to as R482-HEK293) was measured in the absence or presence of Composition 3 (200 µg/ml) (7A) and Composition 2 (200 µg/ml) (7B) or 3 µM of known ABCG2 inhibitor Ko143, followed by analyzing immediately via flow cytometry.

Example 9: ELISA Studies of IL-1 β Expression in THP-1 Macrophages

THP-1 monocyte differentiation was induced by phorbol myristate acetate (PMA). Briefly, cells were pretreated with drugs for 1 hour. After treatment, cell medium was harvested. In supernatants samples, total human IL-1 beta and TNF alpha levels were determined by using enzyme-linked immunosorbent assay (ELISA) kit (eBioscience 88-7010-88 and eBioscience 88-7346-88). Samples (50 µl) were added into a 96-well plate, pre-coated with indicated cytokines monoclonal antibodies respectively and incubated at room temperature for 2 hours. After washing with PBST, secondary antibody was added, and the plate was incubated for 1 hour at room temperature. After washing, 100 µl Avidin-HRP solution was added and incubated for 30 mins at room temperature. After washing, 100 µl/well substrate solution was added and incubated at room temperature in the dark. The reaction was stopped by adding $H_3PO_4$, and the optical density (OD) value was measured at 450 nm.

As shown in the FIGS. 8A-D, Composition 4 treatment alone increased the production of IL-1 β expression in human THP-1 macrophages (8A). Composition 4 can stimulate IL-1β after treated with LPS (8B). Composition 4 treatment alone increased the production of TNF-α expression in human THP-1 macrophages (5C). Composition 4, especially at higher concentration, suppressed LPS-stimulated of TNF-α expression (5D), which suggests that Composition 4 can stimulate immune system (immune response). Composition 4, especially at higher concentration, significantly suppressed LPS-stimulated TNF-α expression, indicating that Composition 4 may exhibit anti-inflammation effect. Interestingly, both Composition 4 and AM-Decoction-DMSO alone increased TNF-α expression in human THP-1 macrophages. Surprisingly, Composition 4 was more potent than AM-Decoction-DMSO. These results suggest that both AM-Decoction-DMSO and Composition 4 (and the like) can stimulate immune system (immune response) (FIG. 8A-D). AM-Decoction-DMSO and exemplary invention composition, Composition 4, especially at higher concentration significantly suppressed LPS-stimulated TNF-α expression, indicating that both invention compositions (such as Composition 4) and AM-Decoction-DMSO exhibit anti-inflammation effect. Taken together, these data suggest that Composition 4 and AM-Decoction-DMSO may augment the immune system and function as an immune-modulator or immunotherapy drug.

Example 10: Studies of Lipolysis and Adipocyte Differentiation in 3T3-L1 Adipocytes by Compositions 2 and 3

Differentiated 3T3-L1 adipocytes were incubated in serum-free medium for 6 hrs, and the glycerol concentration in the medium was measured after treatment for 24 hrs. The effect of Compositions 2 and 3 on the changes in triglyceride accumulation during the processes of adipocyte differentiation and adipocyte fatty acid binding protein (AP2) expression were determined in the Table x.

TABLE 3

Effect of Composition 2 and 3 on lipolysis and adipocyte differentiation in 3T3-L1 adipocytes

|  | | Differentiation | |
| --- | --- | --- | --- |
|  | Lipolysis Glycerol release | Adipocyte fatty acid binding protein (AP2) expression | Triglyceride content |
| Control | 1 | 1 | 1 |
| Composition 2 | 0.62 | 2.29 | 1.09 |
| Composition 3 | 0.68 | 1.10 | 1.45 |

Notes:
AP2 expression > 1 or triglyceride content > 1: These drugs have potential to enhance differentiation of adipocyte. AP2 expression > 1 or triglyceride content > 1: These drugs have potential to enhance differentiation of adipocyte.

3T3-L1 preadipocytes were used to examine the drug potential effects on preadipocyte proliferation and adipocyte differentiation. Cell signal molecules activation cause hydrolysis of triglyceride (TG) to free fatty acids (FFAs) and glycerol. The contribution of adipose tissue browning will stimulate lipolysis in adipocytes leading to achexia. Moreover, many clinic cancer patients have weight loss with atrophy of fat, called cancer cachexia syndrome. When glycerol release in the culture medium was measured as an index of lipolysis. According our results, it was found Composition 2 and Composition 3 can enhance differentiation of adipocyte and inhibit adipocyte to resolve decomposition. That shows promising for improving cancer cachexia and prolonging patient survival.

Example 11: Tube Formation Assay of Composition 3 in HUVEC Cells

Tumor microenvironment is composed of immune cells, cytokines, blood vessels and tumor cells. The complicated interactions in the tumor microenvironment support the tumorigenicity.

Tube formation assay was used to test the inhibitory effect of Composition 3 (400 and 600 μg/ml) in HUVEC cells. Treatment of sorafenib was used as a positive control. The representative images are shown in FIGS. 9A-C. FIG. 9A shows that Composition 3 caused a dose-dependent inhibition of angiogenesis compared to the control group. 600 μg/ml of Composition 3 has a significant inhibition on tube formation after the quantitated after the quantitated by calculating the pentagonal ring or hexagonal ring loop numbers of each well and used solvent control (DMSO) as 100% (FIG. 9B). All samples were assayed in triplicate. Four images were taken per well of a 96-well plate at 10×. The data were quantitated by calculating the pentagonal ring or hexagonal ring loop numbers of each well and used solvent control (DMSO) as 100%.

In the array analysis and preliminary data showed that Composition 3 may play an important role in immune regulation. In addition to the study of the immune modulator role of Composition 3, whether Composition 3 might affect angiogenesis was also studied. To investigate the anti-angiogenesis ability of Composition 3, the effect of Composition 3 on HUVEC cells tube formation was first tested. In the normal condition, HUVEC cells will arrange into pentagon or hexagon shape in matrigel to form a tube. After treating with sorafenib 10 μM (as a positive control) and Composition 3, the number of complete pentagon or hexagon tube was significant decreased.

Example 12: Preclinical Anti-Tumor Evaluation of Compositions 1, 2 and 3 in H441 Xenograft Mouse Model H441 xenograft mouse model was used to comparatively evaluate the anti-tumor effect of Compositions 1-3.

Human lung cancer cell line NCI-H441 (purchased from ATCC, 1 million cells/injection) were subcutaneously injected into the right flank of NOD/SCID mice (female, 4-6 weeks old) and allowed one-two week for tumor growth. One week post injection, tumor-bearing mice were randomly divided into control group (DMSO vehicle) and Chinese herb medicine treatment group (Composition1, 200 mg/kg, 5 days/week; Composition2, 200 mg/kg, 5 days/week; Composition 3, 200 mg/kg, 5 days/week, oral administration). Over the period of 9 weeks, tumorigenesis in both groups was measured using a caliper on a weekly basis. The change in tumor size was expressed as in fold change and plotted over time. (see FIG. 10A)

Human lung cancer cell line NCI-H441 (purchased from ATCC, 1 million cells/injection) were subcutaneously injected into the right flank of NOD/SCID mice (female, 4-6 weeks old) and allowed one-two week for tumor growth. One week post injection, tumor-bearing mice were randomly divided into control group (DMSO vehicle) and Chinese herb medicine treatment group (Composition 1, 3 g/kg, 5 days/week; oral administration; cisplatin, 1 mg/kg, 2 times/week, i.v injection). Over the period of 8 weeks, tumorigenesis in both groups was measured using a caliper on a weekly basis. The change in tumor size was expressed as in fold change and plotted over time as shown in FIG. 10B.

Figure 10C:
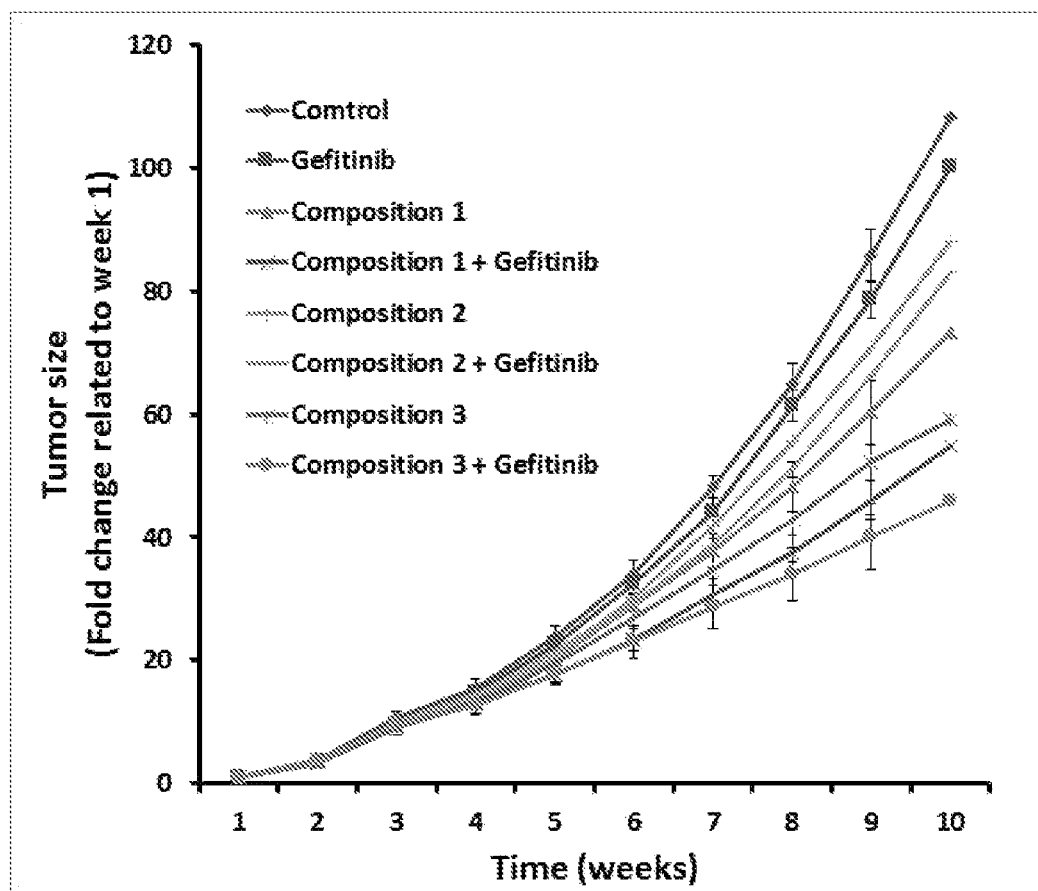

Tumorigenesis was most significantly suppressed in mice which received Composition 3 (200 mg/kg; oral gavage) (10A). In a drug combination experiment, Composition 1-mediated inhibitory effect on the tumor size was measured and judged by the fold changes; the inhibitory effect was ranked in decreasing order as the follows: control, cisplatin, Composition 1 combined with Cisplatin (A-E referred to different brands of Composition 1, FIG. 10B). Drug combination (Composition 1, 2, 3+gefitinib) was examined on CL97 (gefitinib resistance cell line) xenograft model as shown in FIG. 10C.

Example 13: Animal Study of CL97 Xenograft Tumors

Human lung cancer cell line CL97 (obtained from Dr. Pan-Chyr Yang's lab, 1 million cells/injection) were subcutaneously injected into the right flank of NOD/SCID mice (female, 4-6 weeks old) and allowed one-two week for tumor growth. One week post injection, tumor-bearing mice were randomly divided into control group (DMSO vehicle) and Chinese herb medicine treatment group (Composition 1, 1 g/kg, 5 days/week; Composition 2, 600 mg/kg, 5 days/week; Composition 3, 150 mg/kg, 5 days/week, oral administration; gefitinib, 100 mg/kg, 2 times/week, oral administration). Over the period of 10 weeks, tumorigenesis in both groups was measured using a caliper on a weekly basis. The change in tumor size was expressed as in fold change and plotted over time.

(FIG. 10C) Drug combination (Composition 1, 2, 3+gefitinib) was examined on CL97 (gefitinib resistance cell line) xenograft model. The tumor growth inhibitory effect was ranked in decreasing order as the follows: control, Gefitinib, Composition 2, Composition 2 combined with Gefitinib, Composition 1, Composition 3, Composition 1 combined with Gefitinib and Composition 3 combined with Gefitinib). The animals (NOD/SCID mice) were divided into 8 groups (see Table 4), namely control, Gefitinib (100 mg/kg), Composition 1 (1 g/kg), Composition 1+Gefitinib, Composition 2 (600 mg/kg), Composition 2+Gefitinib, Composition 3 (150 mg/kg) and Composition 3+Gefitinib.

Figure 11:
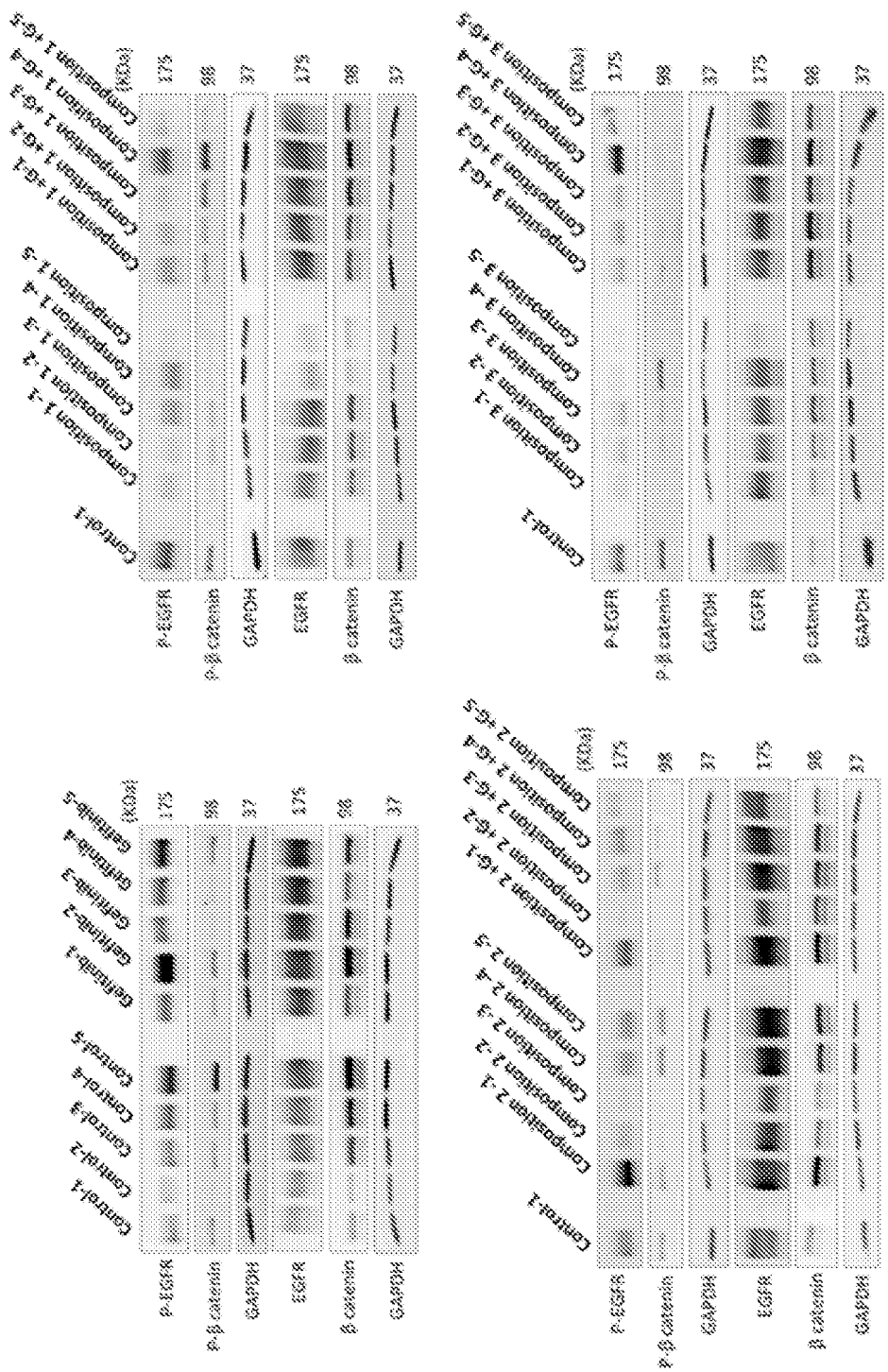
FIG. 11 show illustrative results of a CL97 xenograft tumor study with Compositions 1 and 3.

As shown in the Table 4 and FIG. 11, P-EGFR/EGFR was decreased in Composition 1, Composition 1+Gefitinib, Composition 2+Gefitinib, Composition 3 and Composition 3+Gefitinib. The criteria of quantification: higher than control (1.3 fold change) is up-regulated and lower than control (0.7 fold change) is down-regulated. (n=5, each mice was label as −1, −2, −3, −4, and −5.)

TABLE 4

Summary of animal study results by combination therapy of Compositions 1, 2, or 3
with or without Gefitinib (Composition 1: C1; Composition 2: C2; Composition 3: C3)

|  | Control N = 5 | Gefitinib N = 5 | C2 N = 5 | C2 + Gefitinib N = 5 | C1 N = 5 | C1 + Gefitinib N = 5 | C3 N = 5 | C3 + Gefitinib N = 5 |
|---|---|---|---|---|---|---|---|---|
| P-value |  | 0.2934 | 0.1282 | 0.0118 | 0.0068 | 8.8804E−05 | 0.0028 | 9.18375E−05 |
| Tumor reduction (%) | 0% | 8.8% | 22.0% | 25.0% | 37.0% | 43.0% | 49.2% | 57.6% |
| P-EGFR (Y1068) | 1.00 | 1.70 | 0.79 | 0.40 | 0.33 | 0.37 | 0.24 | 0.54 |
| EGFR | 1.00 | 1.74 | 0.81 | 0.69 | 0.52 | 0.85 | 0.98 | 1.69 |
| p-EGFR/ EGFR | 1.00 | 0.98 | 0.98 | 0.63 | 0.44 | 0.58 | 0.24 | 0.32 |

Criteria: Up regulation fold change >1.3, Down regulation fold change <0.7

Example 14: Clinical Study of Composition 1 on Advanced NSCLC Patients

The investigators aim to study the role of Composition 1 in reversing the immune alterations in patients with advanced stage, non-small cell lung cancer who receive 1st line doublet chemotherapy of cisplatin plus doxetaxel (or Pemetrexed for adenocarcinoma) and 2nd line target therapy of erlotinib. The investigators explore the possible mechanism of the Composition 1 in modulating and reversing immunosuppression in advanced stage, non-small cell lung cancer patients.

This study enrolled 93 patients, including a study group of 62 patients and a control group of 31 patients. We were planning a study with 0.5 controls per experimental subject, an accrual interval of 900 time units, and additional follow-up after the accrual interval of 730 time units. Prior data indicates that the median survival time over the control group treatment is 360 time units. If the true median survival times on the control and experimental treatments are 360 and 730 time units, respectively, this study will need 62 experimental subjects and 31 control subjects to be able to reject the null hypothesis that the experimental and control survival curves are equal with probability (power) 0.800. The Type I error probability associated with this test of this null hypothesis is 0.05.

| Condition | Intervention | Phase |
|---|---|---|
| Carcinoma, Non-Small-Cell Lung | Drug: Composition 1 | Phase 2 Phase 3 |

| Arms | Assigned Intervention |
|---|---|
| Experimental: Composition 1 + standard therapy Composition 1: 7.2 gm BID during 1st line chemotherapy and 2nd line target therapy, maximal for 6 months. 1st line doublet chemotherapy: Cisplatin 70 mg/m2 + Taxotere 60 mg/m2 D1/Q3W x 6 cycles, and then 2nd line target therapy: Erlotinib 150 mg QD. No Intervention: 1st line doublet chemotherapy | Drug: Composition 1 Composition 1: 7.2 gm BID during 1st line chemotherapy and 2nd line target therapy. maximal for 6 months |
| 1st line doublet chemotherapy: Cisplatin 70 mg/m2 + Taxotere 60 mg/m2 D1/Q3W x 6 cycles, and then 2nd line target therapy: Erlotinib 150 mg QD. | |

Study type: interventional
Study design: allocation: randomized
Endpoint classification: safety/efficacy study
Intervention model: parallel assignment
Masking: single blind (outcomes assessor)
Primary purpose: treatment
Primary outcome measures: Overall survival [Time Frame: 3 years] [Designated as safety issue: Yes]
Secondary outcome measures:
Progression-free interval other outcome measures
Quality of life
Safety profile
Inclusion Criteria:
1. Patients with pathological diagnosis of primary non-small-cell lung cancer stage IIIB, IV
2. Age ≥18 years
3. Written, informed consent
4. ECOG: 0-1
Exclusion Criteria:
1. Subjects with inflammatory, infectious or immune disorder, such as TB, AIDS, active pneumonia, DM, SLE, rheumatoid disease.
2. Subjects with systemic organ disease, such as CHF, ESRD, hepatitis, liver cirrhosis.
3. Subjects with malignancy other than NSCLC.
4. Subjects receiving anti-inflammatory or immunosuppressor medications, such as steroid (oral, except for chemotherapy premedication, or inhaled), NASIDs.
5. Patients with no willing to sign the informed consent.
FIG. 17 shows Study Protocol (1) and Study Protocol (2).

In accordance with the protocol, 59 patients with advanced or metastatic stage NSCLC were enrolled for analysis (Table 5) where 38 patients with mean age of 59.28 years, ranged from 37 to 77 years, had received platinum-based doublet chemotherapy in combination with Composition 1; and 21 patients with mean age of 59.35 years, ranged from 43 to 74, had only chemotherapy. Among them, 4 patients (6.8%) were stage IIIB and 55 (93.2%) patients were stage IV. The distribution showed no difference at the time of allocation for study (Table 5).

TABLE 5

Patient Selection Data

| Characteristics | Chemotherapy + Composition 1 | Chemotherapy | P value |
|---|---|---|---|
| EGFR mutation | | | 0.9711 |
| L858R | 7 | 3 | |
| Exon 19 deletion | 7 | 3 | |
| Rare but sensitive mutations | 0 | 0 | |
| T790M | 0 | 0 | |
| Wild type | 22 | 13 | |
| N/A | 2 | 2 | |
| 1st line chemotherapy | | | |
| Platinum (Cisplatin/Carboplatin) | 38/0 | 21/0 | 0.3788 |
| Taxane (Paclitaxel/Docetaxel) | 29 | 16 | |
| Vinorelbine | 0 | 1 | |
| Pemetrexed | 9 | 4 | |
| Others | 0 | 0 | |
| 2$^{nd}$ line therapy | | | 0.6213 |
| Chemotherapy | 6 | 4 | |
| EGFR-TKI Gefitinib/Erlotinib | 23 | 10 | |
| None | 9 | 7 | |
| Patients, No. | 38 | 21 | |
| Age, yr, mean ± SD | 60 | 60.33 | 0.8939 |
| Gender (male/female) | 26/12 | 17/4 | 0.3702 |
| Stage (IIIB/IV) | 2/36 | 2/19 | 0.6185 |
| ECOG (0/1) | 0/38 | 0/21 | |
| Smoking (Never/Former/Current) | 20/13/5 | 5/11/5 | 0.0975 |
| Histology | | | 0.7083 |
| Adenocarcinoma | 29 | 15 | |
| Squamous cell carcinoma | 4 | 2 | |
| Large cell carcinoma | 1 | 2 | |
| Other NSCLC | 4 | 2 | |
| Comorbidity (With/Without) | 22/16 | 12/9 | 1.0000 |

Clinical Trial Results

FIGS. 12A-G show the clinical trial results of progression-free survival (12A), overall survival (12B), overall survival in lung adenocarcinoma (12C), overall survival in lung Non-adenocarcinoma (12D), lung adenocarcinoma wild type overall survival (12E), lung adenocarcinoma with EGFR Mutation overall survival (12F), and after first-line therapy survival (after RECIST-PD survival, 12G).

Figure 12G:
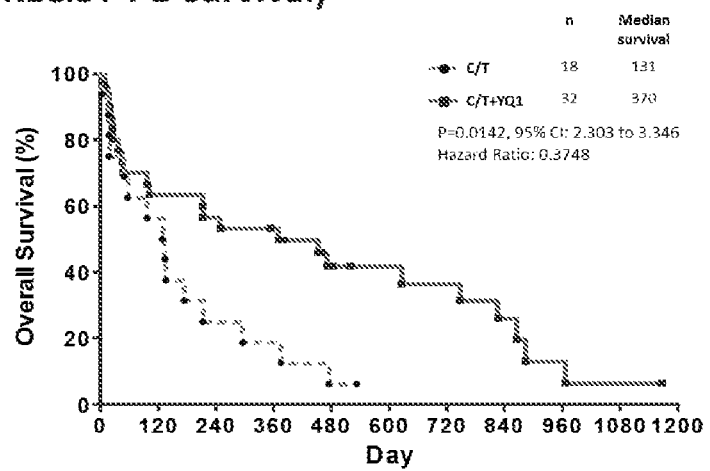

There was no difference in the incidence of adverse events following at least 2 cycles of 1 st line chemotherapy. The median PFS (progression free survival) of the first line platinum-based chemotherapy was 180 days for patients receiving Composition 1, and was 150 days for the control group (95% CI: 0.6568-1.776, p=0.0224) (FIG. 12A). The median OS was 641 days and 284 days for the Composition 1 and control groups, respectively (95% CI: 1.699~2.816, p=0.006) (FIG. 12B). The median OS in lung adenocarcinoma was 844 days and 161 days for the Composition 1 and control groups, respectively (p=0.004) (FIG. 12C). The median OS in lung non-adenocarcinoma was 209.5 days and 221 days for the Composition 1 and control groups, respectively (p=0.5417) (FIG. 12D). The median OS in lung wild-type adenocarcinoma was 198 days and 117 days for the Composition 1 and control groups, respectively (p=0.0137) (FIG. 12E). The median OS in EGFR mutation lung adenocarcinoma was 971 days and 374 days for the Composition 1 and control groups, respectively (p=0.0063) (FIG. 12F). The median OS in After first-line therapy (Response Evaluation Criteria in Solid Tumors-Progression Disease) was 370 days and 131 days for the Composition 1 and control groups, respectively (p=0.0142) (FIG. 12G).

Thus, it is clearly demonstrated that exemplary invention compositions such as Composition 1 improved the efficacy of cisplatin-based chemotherapy in NSCLC, especially in lung adenocarcinoma with EGFR mutation. There was statistical significance between Composition 1 combined with chemotherapy and control group.

Example 15: Flow Cytometry Analysis

Cells were seeded in 6 cm dish with 5×10$^5$ cells per dish for 1 day. Tested drugs were added 24 hours after seeding of the cells and incubated for 24 or 48 hours. Cells were fixed in cold 100% ethanol at 4° C. for overnight and the cell pellets were incubated in a solution containing 20 µg/mL propidium iodide, 0.2 mg/mL RNase, and 0.1% Triton X-100 at room temperature for 15 min. The cells were maintained on ice until analysis by flow cytometry.

Figure 13:
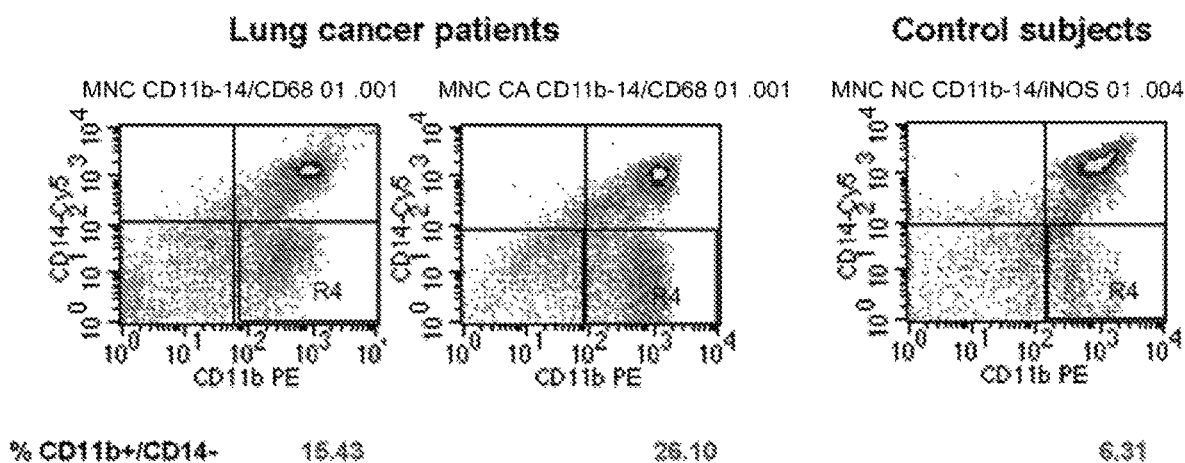
FIG. 13 shows a representative flow cytometry analysis result of expression of myeloid-derived suppressor cells in non-small cell lung cancer patients and control subjects. The population of myeloid suppressor cells (CD11b$^+$/CD14$^-$) was measured.

The population of myeloid suppressor cells (CD11b$^+$/CD14$^-$) was increased in the patients with non-small cell lung cancer compared to control subjects, based on the data shown by flow cytometry. See FIG. 13.

The monocyte M1-like and M2-like subtypes can be identified using flow cytometry. Based on flow cytometry, the CD14+.iNOS$^{high}$ cells are defined as M1 monocytes, and the CD14+/iNOS$^{low}$ cells are defined as M2 monocytes via flow cytometric analysis.

Figure 14:
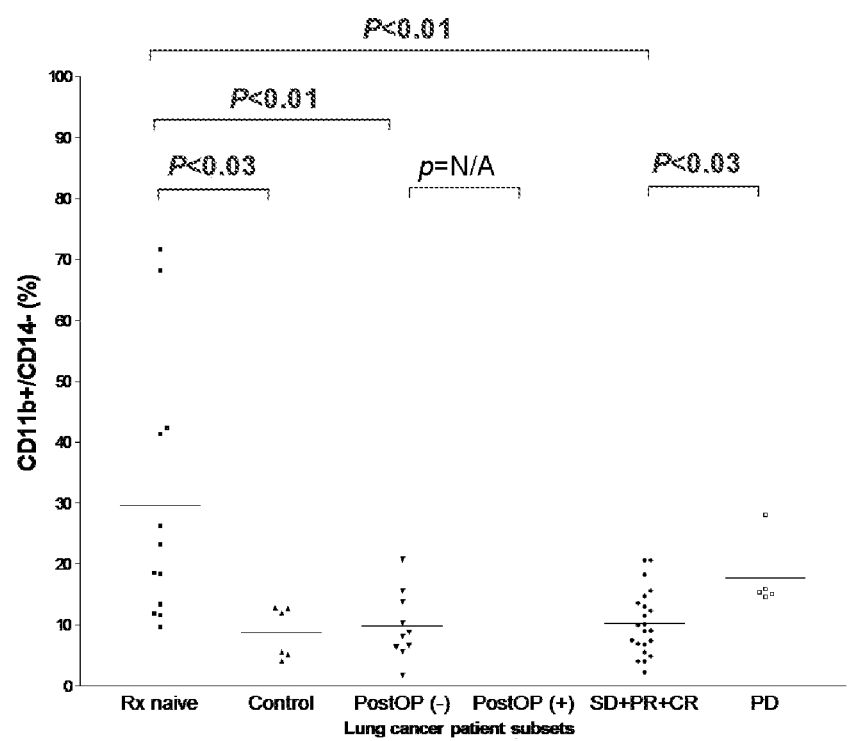
FIG. 14 shows a representative study result of the expression of myeloid suppressor cells in NSCLC patients and control subjects. The number of CD11b+/CD14− mononuclear cells was measured.

As seen in FIG. 14, the number of CD11b+/CD14− mononuclear cells was significantly increased in the treatment-naïve NSCLC patients, compared to control subjects. Furthermore, the population of the cells was significantly decreased in the patient subgroups, who were responsive to chemotherapy/target therapy, or who had received surgery and had no evidence of tumor recurrence at study. Notes: Rx naïve represents treatment-naïve NSCLC patients, Control: control subjects, Post OP (−): early stage operable NSCLC patients with no evidence of recurrence after surgery at study, Post OP (+): initially early stage operable NSCLC patients with recurrence after surgery at study (no patient recruited at pilot study and no data available for preliminary analysis), SD: stable disease, PR: partial response, CR: complete response, PD: progressive disease, according to RECIST (Response Evaluation Criteria in Solid Tumors).

Figure 15:
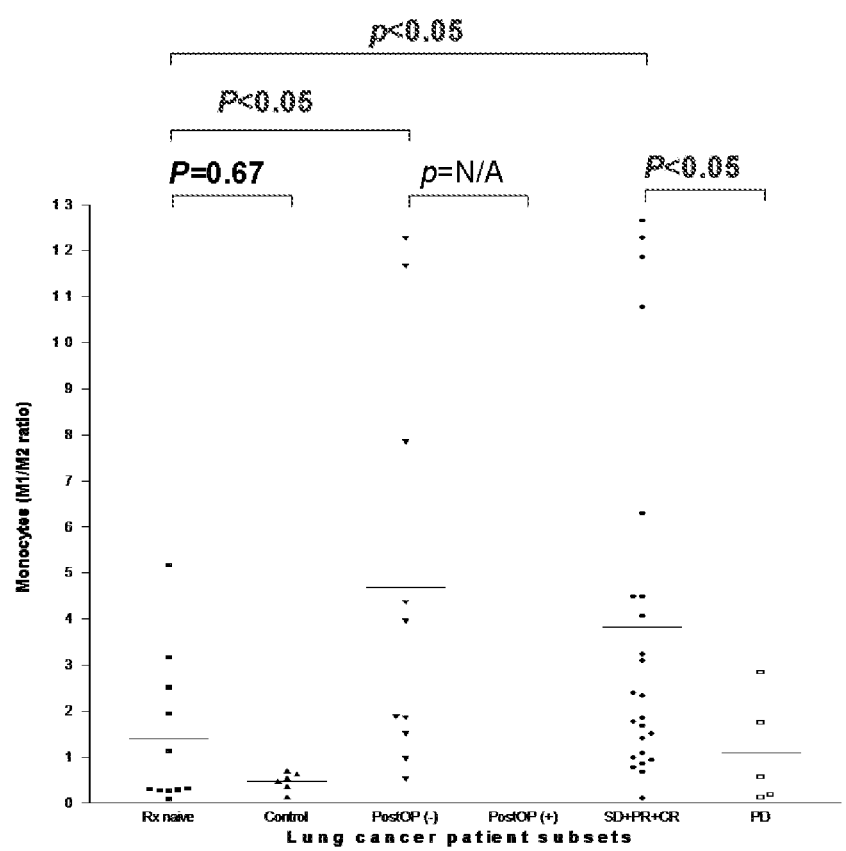
FIG. 15 shows a representative study result of the alteration of monocyte M1 and M2 subtype ratio in the NSCLC patients and control subjects. The range of monocyte M1/M2 ratio was measured.

As shown in FIG. 15, the range of monocyte M1/M2 ratio was increased in the treatment-naïve NSCLC patients, compared to a narrow range of M1/M2 in control subjects. The M1/M2 ratio was significantly increased in the patient subgroups, who were responsive to chemotherapy/target therapy, or who had received surgery and had no evidence of tumor recurrence at study. Notes: Rx naïve represents treatment-naïve NSCLC patients, Control: control subjects, Post OP (−): early stage operable NSCLC patients with no evidence of recurrence after surgery at study, Post OP (+): initially early stage operable NSCLC patients with recurrence after surgery at study (no patient recruited at pilot study and no data available for preliminary analysis), SD: stable disease, PR: partial response, CR: complete response, PD: progressive disease, according to RECIST (Response Evaluation Criteria in Solid Tumors).

Figure 16:
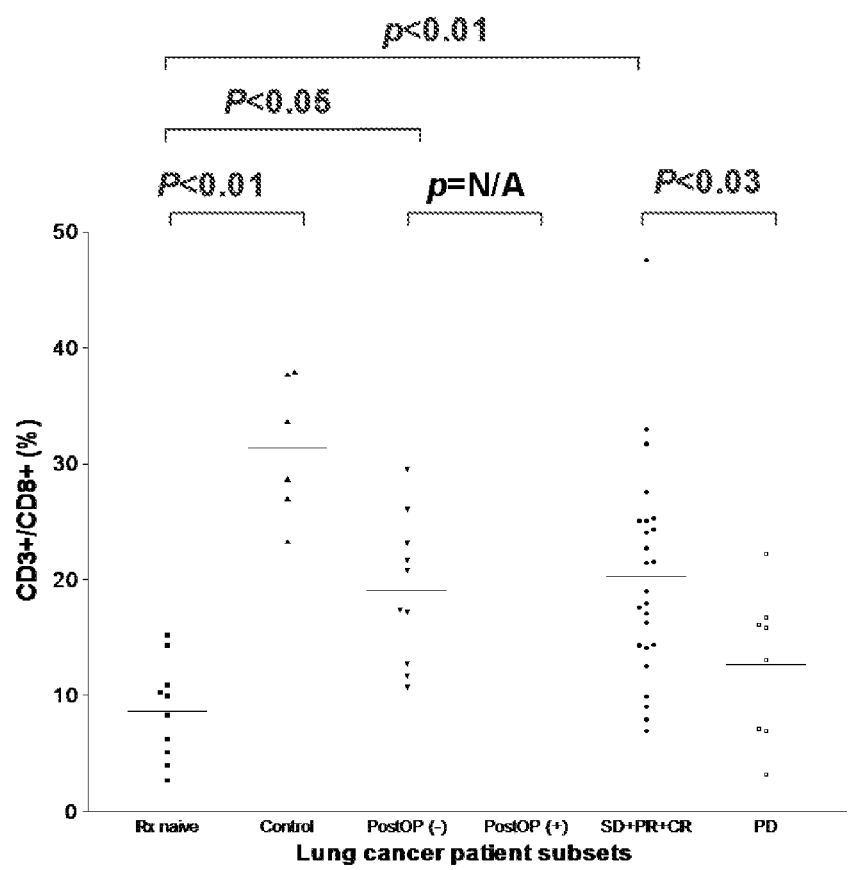
FIG. 16 shows a representative study result of the population of cytotoxic T cells in NSCLC patients and control subjects. The number of CD3+/CD8+ mononuclear cells was measured.

As shown in FIG. 16, the number of CD3+/CD8+ mononuclear cells was significantly decreased in the treatment-naïve NSCLC patients, compared to control subjects. Furthermore, the population of the cells was significantly increased in the patient subgroups, who were responsive to chemotherapy/target therapy, or who had received surgery and had no evidence of tumor recurrence at study. Notes: Rx naïve represents treatment-naïve NSCLC patients, Control: control subjects, Post OP (−): early stage operable NSCLC patients with no evidence of recurrence after surgery at study, Post OP (+): initially early stage operable NSCLC patients with recurrence after surgery at study (no patient recruited at pilot study and no data available for preliminary analysis), SD: stable disease, PR: partial response, CR: complete response, PD: progressive disease, according to RECIST (Response Evaluation Criteria in Solid Tumors).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An extended release composition consisting essentially of:
   extracts of *Astragalus, Cimicifuga foetida rhizoma, Ophiopogon radix, Atractylodes lancea rhizoma, Panax ginseng*-Red, *Atractylodes rhizoma*-White, *Massa medicata fermentata, Citrus reticulata-viride, Citrus reticulata, Glycyrrhiza radix, Schisandra fructus, Angelica sinensis radix, Phellodendron cortex, Alisma rhizoma, Pueraria radix, Ziziphus fructus*-Red, and *Zingiber officinale radix*; and
   a cytotoxic agent selected from the group consisting of tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, 13-Deoxydoxorubicin, (trans, trans, trans)-bis-mu-(hexane-1,6-diamine)-mu-[diamine-platinum(II)]bis [diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, sabarubicin hydrochloride, and 4-demethoxy-3-deamino-3-aziridinyl-4-methylsulphonyl-daunorubicin and combinations thereof.

2. The extended release composition of claim 1, wherein the cytotoxic agent is cisplatin.

3. The extended release composition of claim 2, which improves the efficacy of cisplatin-based therapy.

4. The extended release composition of claim 1, which increases the production of IL-1β expression.

5. The extended release composition of claim 1, which increases the production of TNF-α expression.

6. An extended release composition consisting essentially of:
   extracts of *Astragalus, Cimicifuga foetida rhizoma, Ophiopogon radix, Atractylodes lancea rhizoma, Panax ginseng*-Red, *Atractylodes rhizoma*-White, *Massa medicata fermentata, Citrus reticulata-viride, Citrus reticulata, Glycyrrhiza radix, Schisandra fructus, Angelica sinensis radix, Phellodendron cortex, Alisma rhizoma, Pueraria radix, Ziziphus fructus*-Red, and *Zingiber officinale radix*; and
   a tyrosine kinase inhibitor is selected from the group consisting of afatinib, erlotinib, osimertinib, [4-(3-chloro-2-fluoroanilino)-7-methoxyquinazolin-6-yl] (2R)-2,4-dimethylpiperazine-1-carboxylate, gefitinib, canertinib, lapatinib, cetuximab, matuzumab, zalutumumab, panitumumab and combinations thereof.

7. The extended release composition of claim 6, wherein the tyrosine kinase inhibitor is gefitinib.

8. The extended release composition of claim 6, which improves the efficacy of tyrosine kinase inhibitor.

9. The extended release composition of claim 6, which increases the production of IL-1β expression.

10. The extended release composition of claim 6, which increases the production of TNF-α expression.

* * * * *